US011970540B2

(12) United States Patent
Trinklein et al.

(10) Patent No.: US 11,970,540 B2
(45) Date of Patent: Apr. 30, 2024

(54) ANTI-BCMA HEAVY CHAIN-ONLY ANTIBODIES

(71) Applicant: TENEOBIO, INC., Thousand Oaks, CA (US)

(72) Inventors: Nathan Trinklein, Thousand Oaks, CA (US); Shelley Force Aldred, Thousand Oaks, CA (US); Katherine Harris, Thousand Oaks, CA (US); Wim van Schooten, Thousand Oaks, CA (US)

(73) Assignee: TENEOBIO, INC., Thousand Oaks, CA (US)

( * ) Notice: Subject to any disclaimer, the term of this patent is extended or adjusted under 35 U.S.C. 154(b) by 474 days.

(21) Appl. No.: 16/622,881

(22) PCT Filed: Jun. 20, 2018

(86) PCT No.: PCT/US2018/038549
§ 371 (c)(1),
(2) Date: Dec. 13, 2019

(87) PCT Pub. No.: WO2018/237037
PCT Pub. Date: Dec. 27, 2018

(65) Prior Publication Data
US 2021/0147564 A1 May 20, 2021

Related U.S. Application Data

(60) Provisional application No. 62/522,355, filed on Jun. 20, 2017.

(51) Int. Cl.
C07K 16/28 (2006.01)

(52) U.S. Cl.
CPC ...... C07K 16/2878 (2013.01); C07K 16/2809 (2013.01); C07K 2317/31 (2013.01); C07K 2317/51 (2013.01)

(58) Field of Classification Search
None
See application file for complete search history.

(56) References Cited

U.S. PATENT DOCUMENTS

| 4,816,567 | A | 3/1989 | Cabilly et al. |
|---|---|---|---|
| 5,500,360 | A | 3/1996 | Ahlquist et al. |
| 5,500,362 | A | 3/1996 | Robinson et al. |
| 5,585,097 | A | 12/1996 | Bolt et al. |
| 5,821,337 | A | 10/1998 | Carter et al. |
| 5,929,212 | A | 7/1999 | Jolliffe et al. |
| 5,968,509 | A | 10/1999 | Gorman et al. |
| 6,706,265 | B1 | 3/2004 | Bolt et al. |
| 6,750,325 | B1 | 6/2004 | Jolliffe et al. |
| 7,262,276 | B2 | 8/2007 | Huang et al. |
| 7,381,803 | B1 | 6/2008 | Weiner et al. |
| 7,541,513 | B2 | 6/2009 | Brüggeman et al. |
| 7,635,472 | B2 | 12/2009 | Kufer et al. |
| 7,728,114 | B2 | 6/2010 | Mach et al. |
| 7,862,813 | B2 | 1/2011 | Bjork et al. |
| 8,106,163 | B2 | 1/2012 | Heusser et al. |
| 8,207,303 | B2 | 6/2012 | Cardarelli et al. |
| 8,236,308 | B2 | 8/2012 | Kischel et al. |
| 8,367,888 | B2 | 2/2013 | Brügemann et al. |
| 8,883,150 | B2 | 11/2014 | Craig et al. |
| 9,034,324 | B2 | 5/2015 | Kalled et al. |
| 9,096,651 | B2 | 8/2015 | Igawa et al. |
| 9,150,664 | B2 | 10/2015 | Kufer et al. |
| 9,340,621 | B2 | 5/2016 | Kufer et al. |
| 9,365,655 | B2 | 6/2016 | Craig et al. |
| 9,228,016 | B2 | 11/2016 | Wang et al. |
| 9,587,036 | B2 | 3/2017 | Kufer |
| 9,765,342 | B2 | 9/2017 | Kochenderfer |
| 10,202,452 | B2 | 2/2019 | Tan et al. |
| 10,465,009 | B2 | 11/2019 | Armitage et al. |
| 10,465,010 | B2 | 11/2019 | Wang et al. |
| 10,934,363 | B2 | 3/2021 | Fan et al. |
| 2004/0229310 | A1 | 11/2004 | Simmons |
| 2005/0048572 | A1 | 3/2005 | Reilly et al. |
| 2007/0065437 | A1 | 3/2007 | Elson et al. |
| 2007/0071675 | A1 | 3/2007 | Wu et al. |
| 2007/0212733 | A1 | 9/2007 | Martin |
| 2009/0098134 | A1 | 4/2009 | Buelow |
| 2010/0122358 | A1 | 5/2010 | Brüggemann et al. |
| 2010/0150918 | A1 | 6/2010 | Kufer |
| 2011/0293619 | A1 | 12/2011 | Kufer et al. |
| 2013/0101599 | A1 | 4/2013 | Borages et al. |
| 2013/0156769 | A1 | 6/2013 | Kufer et al. |
| 2013/0273055 | A1 | 10/2013 | Borges et al. |

(Continued)

FOREIGN PATENT DOCUMENTS

| CN | 105384825 | 3/2016 |
|---|---|---|
| CN | 105457024 A | 4/2016 |

(Continued)

OTHER PUBLICATIONS

Salazar-Camarena et al. (Lupus (2016) 25, 582-592). (Year: 2016).*
Janssens et al., "Generation of Heavy-chain-only Antibodies in Mice," (2006) PNAS 102(41):15130-15135.
Ryan et al., "Antibody targeting of B-celll maturation antigen on malignant plasma cells," (2007) Mol Cancer Ther 6(11):3009-3018.
Kontermann, "Invited review—Recombinant bispecific antibodies for cancer therapy," (2005) Acta Pharmacologica Sinica 26(1):1-9.
Novak et al., "Expression of BCMA, TACI, and BAFF-R in multiple myeloma: a mechanism for growth and survival," (2004) Blood 103(2):689-694.
Sequence Listing of PCT Publication No. WO 2009/132058 (D2), published Oct. 29, 2009.

(Continued)

Primary Examiner — Zachary S Skelding
(74) Attorney, Agent, or Firm — Haynes and Boone LLP

(57) ABSTRACT

Anti-BCMA heavy chain-only antibodies (UniAb) and disclosed, along with methods of making such antibodies, compositions, including pharmaceutical compositions, comprising such antibodies, and their use to treat B-cell disorders characterized by the expression of BCMA.

14 Claims, 5 Drawing Sheets
Specification includes a Sequence Listing.

(56) References Cited

U.S. PATENT DOCUMENTS

| | | |
|---|---|---|
| 2013/0273066 A1 | 10/2013 | Borges et al. |
| 2013/0280280 A1 | 10/2013 | Algate et al. |
| 2015/0118251 A1 | 4/2015 | Deslandes |
| 2015/0266966 A1 | 9/2015 | Smith et al. |
| 2015/0368351 A1 | 12/2015 | Vu et al. |
| 2015/0376287 A1 | 12/2015 | Vu et al. |
| 2016/0046724 A1 | 2/2016 | Brogdon et al. |
| 2016/0159894 A1 | 6/2016 | Hartmann et al. |
| 2016/0166689 A1 | 6/2016 | Adler et al. |
| 2016/0194399 A1 | 7/2016 | Irving et al. |
| 2016/0355591 A1 | 12/2016 | Goldenberg et al. |
| 2017/0051068 A1 | 2/2017 | Pillarisetti et al. |
| 2017/0081411 A1 | 3/2017 | Engels et al. |
| 2017/0240612 A1 | 8/2017 | Bachmann et al. |
| 2019/0106504 A1 | 4/2019 | Wu et al. |
| 2019/0026390 A1 | 8/2019 | Trinklein et al. |
| 2019/0263904 A1 | 8/2019 | Trinklein et al. |
| 2019/0352412 A1 | 11/2019 | Force Aldred et al. |
| 2020/0048348 A1 | 2/2020 | Trinklein et al. |
| 2020/0078399 A1 | 3/2020 | Fan et al. |
| 2020/0085839 A1 | 3/2020 | Sidransky et al. |
| 2020/0131262 A1 | 4/2020 | Ehninger |
| 2020/0157232 A1 | 5/2020 | Trinklein et al. |
| 2020/0181228 A1 | 6/2020 | Bachmann et al. |
| 2020/0339685 A1 | 10/2020 | Schellenberger et al. |
| 2021/0047402 A1 | 2/2021 | Trinklein et al. |
| 2021/0147564 A1 | 5/2021 | Trinklein et al. |
| 2021/0340255 A1 | 11/2021 | Harris et al. |
| 2022/0025047 A1 | 1/2022 | Trinklein et al. |
| 2022/0089729 A1 | 3/2022 | Harris et al. |

FOREIGN PATENT DOCUMENTS

| | | |
|---|---|---|
| EP | 1210425 B1 | 4/2007 |
| EP | 1223964 B1 | 4/2007 |
| EP | 2762497 A1 | 8/2014 |
| EP | 1806143 B1 | 6/2016 |
| EP | 2780374 B1 | 8/2019 |
| EP | 2780375 B1 | 11/2019 |
| WO | 1996/027011 | 9/1996 |
| WO | 1996/032478 A1 | 10/1996 |
| WO | 1997/034631 A1 | 9/1997 |
| WO | 1998/050431 | 11/1998 |
| WO | 2000/040716 A2 | 7/2000 |
| WO | 2001/012812 A2 | 2/2001 |
| WO | 2001/024811 | 4/2001 |
| WO | 2001/024811 A1 | 4/2001 |
| WO | 2001/024812 | 4/2001 |
| WO | 2001/077342 A1 | 10/2001 |
| WO | 2001/087977 A2 | 11/2001 |
| WO | 2002/066516 | 8/2002 |
| WO | 2002/066516 A2 | 8/2002 |
| WO | 2004/106383 A1 | 12/2004 |
| WO | 2005/040220 A1 | 5/2005 |
| WO | 2005/061547 A2 | 7/2005 |
| WO | 2006/008548 | 1/2006 |
| WO | 2007/042261 A2 | 4/2007 |
| WO | 2007/066109 | 6/2007 |
| WO | 2007/117600 | 10/2007 |
| WO | 2008/119565 A2 | 10/2008 |
| WO | 2008/119566 A2 | 10/2008 |
| WO | 2008/119567 A2 | 10/2008 |
| WO | 2009055669 | 4/2009 |
| WO | 2009/132058 | 10/2009 |
| WO | 2009/132058 A2 | 10/2009 |
| WO | 2010/037835 A2 | 4/2010 |
| WO | 2010/037836 A2 | 4/2010 |
| WO | 2010/037837 A2 | 4/2010 |
| WO | 2010/037838 A2 | 4/2010 |
| WO | 2010/104949 A2 | 9/2010 |
| WO | 2010/109165 A2 | 9/2010 |
| WO | 2011/097603 A1 | 8/2011 |
| WO | 2012/066058 | 5/2012 |
| WO | 2012/066058 A1 | 5/2012 |
| WO | 2012/122512 A1 | 9/2012 |
| WO | 2012/143498 | 10/2012 |
| WO | 2012/163805 | 12/2012 |
| WO | 2013/072406 | 5/2013 |
| WO | 2013/072406 A1 | 5/2013 |
| WO | 2013/072415 | 5/2013 |
| WO | 2013/154760 A1 | 10/2013 |
| WO | 2014/022540 A1 | 2/2014 |
| WO | 2014/047231 A1 | 3/2014 |
| WO | 2014/068079 A1 | 5/2014 |
| WO | 2014/089335 A2 | 6/2014 |
| WO | 2014/093908 A2 | 6/2014 |
| WO | 2014/112144 | 8/2014 |
| WO | 2014/122144 | 8/2014 |
| WO | 2015/095412 A1 | 6/2015 |
| WO | 2015/121383 A1 | 8/2015 |
| WO | 2015/149077 | 10/2015 |
| WO | 2016/014789 A2 | 1/2016 |
| WO | 2016/030414 A1 | 3/2016 |
| WO | 2016/048938 A1 | 3/2016 |
| WO | 2016/062990 A1 | 4/2016 |
| WO | 2016/079081 A1 | 5/2016 |
| WO | 2016/079177 A1 | 5/2016 |
| WO | 2016/094304 A2 | 6/2016 |
| WO | 2016/113555 A1 | 7/2016 |
| WO | 2016/187546 | 11/2016 |
| WO | 2017/025038 A1 | 2/2017 |
| WO | 2017/031104 A1 | 2/2017 |
| WO | 2015/063339 | 5/2017 |
| WO | 2017/081211 | 5/2017 |
| WO | 2017/223111 A1 | 12/2017 |
| WO | 2018/039180 A1 | 3/2018 |
| WO | 2018/052503 A1 | 3/2018 |
| WO | 2018/237006 | 12/2018 |
| WO | 2018/237037 | 12/2018 |
| WO | 2019/000223 | 1/2019 |
| WO | 2019/006072 A1 | 1/2019 |
| WO | 2019/133761 | 7/2019 |
| WO | 2020/018922 A1 | 1/2020 |
| WO | 2020/206330 A1 | 10/2020 |

OTHER PUBLICATIONS

BCMA (Vicky-1): sc-57037 datasheet, Santa Cruz Biotechnology, https://datasheets.scbt.com/sc-57037.pdf (last visited Apr. 12, 2022).
BCMA (Vicky-1): ALX-804-151 product datasheet, Enzo Life Sciences, last revised Dec. 20, 2019.
MAB193 data sheet, Human BCMA/TNFRSF17 Antibody, R&D Systems, last revised Feb. 7, 2018.
Hipp et al., "A novel BCMA/CD3 bispecific T-cell engager for the treatment of multiple myeloma induces selective lysis in vitro and in vivo," (2017) Leukemia 31:1743-1751.
Sequence Listing of PCT Publication No. WO 2008/119567, published Oct. 9, 2008.
GenBank Accession No. AB052772.1, "Homo sapiens gene for BCMA, complete cds," available at https://www.ncbi.nlm.nih.gov/nuccore/AB052772 (last visited Apr. 23, 2020).
Fitzgerald et al., "The Cytokine FactsBook," 2nd ed. (2001) Academic Press, pp. 151-152.
Bossen et al., "Review, BAFF, APRIL and their receptors: Structure, function and signaling," (2006) Seminars in Immunology 18:263-275.
Bodmer et al., "Review—The molecular architecture of the TNF superfamily," (2002) Trends in Biochemical Sciences 27(1):19-26.
Hymowitz et al., "Structures of APRIL-Receptor Complexes," (2005) Journal of Biological Chemistry 280(8):7218-7227.
Liu et al., "Ligand-receptor binding revealed by the TNF family member TALL-1," (2003) Nature 423:49-56.
Wallweber et al., "The Crystal Structure of A Proliferation-inducing Ligand, APRIL," (2004) Journal of Molecular Biology 343:283-290.
Patel et al., "Engineering an APRIL-specific B Cell Maturation Antigen," (2004) Journal of Biological Chemistry 279(16):16727-16735.
Vidal-Laliena et al., "Characterization of antibodies submitted to the B cell section of the 8th human leukocyte differentiation antigens workshop by flow cytometry and immunohistochemistry," (2005) Cellular Immunology 236:6-16.

(56) References Cited

OTHER PUBLICATIONS

Moreaux et al., "APRIL and TACI interact with syndecan-1 on the surface of multiple myeloma cells to form an essential survival loop," (2009) Eur J Heamatol 83:119-129.
Bellucci et al., "Graft-versus-tumor response in patients with multiple myeloma is associated with antibody response to BCMA, a plasma-cell membrane receptor," (2005) Blood 105(10):3945-3950.
Bellucci et al., "Complete response to donor lymphocyte infusion in multiple myeloma is associated with antibody responses to highly expressed antigens," (2004) Blood 103(2):656-663.
Leiba et al., "Activation of B cell maturation antigen (BCMA) on human multiple myeloma cells by a proliferation-inducing ligand (APRIL) promotes myeloma cell function in the bone marrow microenvironment," (2007) Blood 110(11):1503.
Bellucci et al., "Complete response to donor lymphocyte infusion in patients with multiple myeloma is associated with antibody response to BCMA, a plasma cell membrane receptor" (2003) Blood 102(11):192a-193a.
Tarte et al., "BAFF is a survival factor for multiple myeloma cells," Myeloma Biology II: (2002) p. 811a (Abstract #3203).
Dillon et al., "An APRIL to remember: Novel TNF ligands as therapeutic targets," (2006) Nat Rev 5:235-246.
Kontermann "Bispecific Antibodies" (2011), Springer-Verlag Berlin Heidelberg, Chapters 1, 2, 7, 11, 13, 14 and 15.
Supporting evidence that D41 was available in Jul. 2011 and thus before the claimed priority dates.
Choi et al., "Bispecific antibodies engage T-cells for antitumor Immunotherapy," (2011) Expert Opinion on Biological Therapy 11(7):843-853.
Müller et al., "Bispecific antibodies for cancer immunotherapy," (2010) Biodrugs 24(2):89-98.
Thakur et al., "Cancer therapy with bispecific antibodies: Clinical experience," (2010) Current Opinion in Molecular Therapeutics 12(3):340-349.
Chames et al., "Bispecific antibodies for cancer therapy," (2009) Current Opinion in Drug Discovery & Development 12(2):276-283.
Baeuerle et al., "Bispecific T-cell engaging antibodies for cancer therapy," (2009) Cancer Research 69(12):4941-4944.
Baeuerle et al., "BiTE: Teaching antibodies to engage T-cells for cancer therapy," (2009) Current Opinion in Molecular Therapeutics 11(1):22-30.
Baeuerle et al., "BiTE: A new class of antibodies that recruit T-cells," (2008) Drugs of the Future 33(2):137-147.
Muller et al., "Recombinant bispecific antibodies for cellular cancer immunotherapy," (2006) Current Opinion in Molecular Therapeutics 9(4):319-326.
Kufer et al., "Review—A revival of bispecific antibodies," (2004) Trends in Biotechnology 22(5):238-244.
GenBank Accession No. NM_000733, "*Homo sapiens* CD3e molecule (CD3E), mRNA", available at https://www.ncbi.nlm.nih.gov/nuccore/NM_000733.3 (last visited Apr. 23, 2020).
Panowski et al., "Preclinical efficacy and safety comparison of CD3 bispecific and ADC modalities targeting BCMA for the treatment of multiple myeloma," (2019) AACR OF1-OF13.
Declaration of Dr. Rui Zhu, PhD, dated Jun. 9, 2020 in EP Opposition No. 3428193 for EP Application No. 18187373.8.
Declaration of Kevin C. Lindquist in EP Opposition No. 3428193 for EP Application No. 18187373.8.
Excerpt of examination report from EP Application No. 12805432.7, dated Oct. 31, 2016, p. 1.
Patentee's Response to EP Communication under Article 94(3), dated May 10, 2017 in EP Application No. 12805432.7.
Patentee's Response to EP Communication under Article 94(3), dated Apr. 13, 2016 in EP Application No. 12805432.7.
Rennert et al., "A Soluble Form of B Cell Maturation Antigen, a Receptor for the Tumor Necrosis Factor Family Member APRIL, Inhibits Tumor Cell Growth," (2000) J. Exp. Med. 192(11):1677-1683.
Declaration Nathan D. Trinklein, Ph.D. in EP Opposition No. 3428193 for EP Application No. 18187373.8.
Kuhns et al., "Deconstructing the Form and Function of the RCR/CD3 Complex," (2006) Immunity 24:133-139.
Koarada et al., "Autoantibody-Producing RP105 B Cells, from Patients with Systematic Lupus Erythematosus, showed more Preferential Expression of BCMA Compared with BAFF-R than Normal Subject," (2010) Rheumatology 49:662-670.
Pelekanou et al., "Expression of TNF-superfamily members BAFF and APRIL in Breast Cancer: Immunohistochemical Study in 52 Invasive Ductal Breast Carcinomas," (2008) BMC Cancer 8(76):1-9.
Guy et al., "Organization of Proximal Signal at the TCR:CD3 Complex," (2009) Immunol Rev 232(1):1-22.
Proprietor's Remarks in Response to Office Action dated Jun. 19, 2014 in U.S. Pat. No. 9,150,664.
Proprietor's Remarks in Response to Office Action dated Dec. 16, 2014 in U.S. Pat. No. 9,340,621.
Kjer-Nielsen et al., "Crystal Structure of the Human T Cell Receptor CD3 εγ Heterodimer Complexed to the Therapeutic mAb OKT3," (2004) Proceedings of the National Academy of Sciences 101:7675-7680.
Chames et al., "Bispecific Antibodies for Cancer Therapy," (2009) mAbs 1(6):539-547.
Clayton et al., "CD3η and CD3 are alternatively spliced products of a common genetic locus and are transcriptionally and/or post-transcriptionally regulated during T-cell development," (1991) Proceedings of the National Academy of Sciences USA 88:5202-5206.
Neisig et al., "Assembly of the T-Cell Antigen Receptor," (1993) Journal of Immunology 151:870-879.
Bargou et al., "Tumor Regression in Cancer Patients by Very Low Doses of a T Cell-Engaging Antibody," (2008) Science 321:974-977.
Honemann et al., 'A Novel Recombinant Bispecific Single-chain Antibody, bscWue-1 × CD3, Induces T-cell-mediated Cytotoxicity Towards Human Multiple Myeloma Cells, (2004) Leukemia 15:636-644.
Wayback machine snapshot of BCMA UniprotKB/Swiss-Prot entry, Aug. 3, 2011 https://web.archive.org/web/20110803071256/ https://www.uniprot.org/uniprot/Q02223.
Gruss et al., "Structural and Biological Features of the TNF Receptor and TNF Ligand Superfamilies: Interactive Signals in the Pathobiology of Hodgkin's Disease," (1996) Ann Oncol, 7 (Suppl 4):19-26.
Levine, "Mechanisms of Soluble Cytokine Generation," (2004) J Immunol 173(9):5343-8.
Reichert et al., "Development Trends for Monoclonal Antibody Cancer Therapeutics," (2007) Nat Rev Drug Discov 6(5):349-356.
Sanchez et al., "Serum B-cell Maturation Antigen Elevated in Multiple Myeloma and Correlates with Disease Status and Survival," (2012) Br J Haematol 158(6):727-738.
Topp et al., "Anti-B-Cell Maturation Antigen BiTE Molecule AMG 420 Induces Responses in Multiple Myeloma." (2020) J Clin Oncol 38(8):775-783.
Statutory Declaration of Dr. Robert Saller, Executive Director Program Management at Amgen Research (Munich) GmbH (Vice President R&D Operations & Planning in Jan. 2011).
Kapoor et al., "Anti-CD20 Monoclonal Antibody Therapy in Multiple Myeloma," (2008) Br J Haematol 141(2):135-148.
Figure 6.8 of Antigen receptor structure and signaling pathways, Immunobiology: The Immune System in Health and Disease. 5th Edition, Janeway CA Jr, Travers P, Walport M, et al., New York: Garland Science; 2001.
Declaration of Kara Olson, dated May 14, 2021 in EP Opposition No. 3428193 for EP Application No. 18187373.8.
Bluemel et al., "Epitope Distance to the Target Cell Membrane and Antigen Size Determine the Potency of T Cell-mediated Lysis by BiTE Antibodies Specific for a Large Melanoma Surface Antigen," (2010) Cancer Immunol Immunother 59:1197-1209.
Verkleij et al., "T-Cell Redirecting Bispecific Antibodies Targeting BCMA for the Treatment of Multiple Myeloma," (2020) Oncotarget 11(45):4076-4081.
Gras et al., "BCMAp: an integral membrane protein in the Golgi apparatus of human mature B lymphocytes," (1995) International Immunology 7(7):1093-1106.

(56) References Cited

OTHER PUBLICATIONS

Tai et al., "Novel anti-B-cell maturation antigen antibody-drug conjugate (GSK2857916) selectively induces killing of multiple myeloma," (2014) Blood 123(20):3128-3138.
Ali et al., "T cells expressing an anti-B-cell maturation antigen chimeric antigen receptor cause remissions of multiple myeloma," (2016) Blood 128(13):1688-1700.
Muyldermans, "Single domain camel antibodies: current status," (2001) 74(4):277-302.
Revets et al., "Nanobodies as novel agents for cancer therapy," (2005) Expert Opinion on Biological Therapy 5(1):111-124.
Nuttall et al., "Isolation and characterization of an IgNAR variable domain specific for the human mitochondrial translocase receptor Tom70," (2003) Eur. J. Biochem. 270:3543-3554.
Nuttall et al., "Selection and affinity maturation of IgNAR variable domains targeting Plasmodium falciparum AMA1," (2004) Function and Bioinformatics 55(1):187-197.
Dooley et al., "Selection and characterization of naturally occurring single-domain (IgNAR) antibody fragments from immunized sharks by phage display," (2003) Molecular Immunology 40(1):25-33.
Jaton et al., "Recovery of antibody activity on reoxidation of completely reduced polyalanyl heavy chain and its Fd fragment derived from anti-2,4-dinitrophenyl antibody," (1968) Biochemistry, 7(12):4185-4195.
Sitia et al., "Developmental regulation of IgM secretion: The role of the carboxy-terminal cysteine," (1990) Cell 60(5):781-790.
Van der Linden et al., "Comparison of physical chemical properties of llama VHH antibody fragments and mouse monoclonal antibodies," (1999) Biochim. Biophys. Acta. 1431(1):37-46.
Frenken et al., "Isolation of antigen specific Llama $V_{HH}$ antibody fragments and their high level secretion by *Saccharomyces cerevisiae*," (2000) J. Biotechnol. 78(1):11-21.
Ghahroudi et al., "Selection and identification of single domain antibody fragments from camel heavy-chain antibodies," (1997) FEBS Lett. 414(3):521-526.
Nguyen et al., "Heavy-chain only antibodies derived from dromedary are secreted and displayed by mouse B cells," (2003) Immunology; 109(1):93-101.
Brüggemann et al., "Heavy-Chain-Only Antibody Expression and B-Cell Development in the Mouse," (2006) Crit. Rev. Immunol. 26(5):377-90.
Zou et al., "Heavy chain-only antibodies are spontaneously produced in light chain-deficient mice," (2007) J Exp Med 204(13):3271-3283.
Geurts et al., "Knockout Rats via Embryo Microinjection of Zinc-Finger Nucleases," (2009) Science 24(325):433.
Iri-Sofla et al., "Nanobody-based chimeric receptor gene integration in Jurkat cells mediated by PhiC31 integrase," (2011) Experimental Cell Research 317:2630-2641.
Jamnani et al., "T cells expressing VHH-directed oligoclonal chimeric HER2 antigen receptors: Towards tumor-directed oligoclonal T cell therapy," (2014) Biochim Biophys Acta 1840(1):378-386.
Carpenter et al., "B-cell Maturation Antigen Is a Promising Target for Adoptive T-cell Therapy of Multiple Myeloma," (2013) Clin Cancer Res 19(8):2048-2060.
Tai et al., "APRIL and BCMA promote human multiple myeloma growth and immunosuppression in the bone marrow microenvironment," (2016) Blood 127(25):3225-3236.
Sanz et al., "B cells as therapeutic targets in SLE," (2010) Nature Reviews Rheumatology 6:326-337.
Fry et al., "CD22-targeted CAR T Cells Induce Remission in B-ALL that is Naïve or Resistant to CD19-targeted CAR Immunotherapy," (2018) Nature Medicine 24(1):20-28.
Nishimoto et al., "Adoptive Therapy with Cord Blood T Reglatory Cells Enhances Anti-myeloma Efficacy of T Cell Based Immunotherapies," (2020) Blood 136(Supp1); 26-27.
Qin et al., "Paralleled comparison of vectors for the generation of CAR-T cells," (2016) Anti-Cancer Drugs 27(8):711-722.

Rodriguez et al., "Initial Resulst of a Phase I Study of TNB-383B, a BCMA x CD3 Bispecific T-Cell Redirecting Antibody, in Relapsed/Refracotry Multiple Myeloma," (2020) Blood 136 (Supp 1):43-44.
Rouet et al., "Fully Human VH Single Domains that Rival the Stability and Cleft Recognition of Camelid Antibodies," (2015) Journal of Biological Chemistry 290(19):11905-11917.
Ryan et al., :Antibody Targeting of B-Cell Maturation Antigen on Malignant Plasma Cells, (2007) Mol Cancer Ther 6(11):3009-3018.
Van Schooten et al., "A Novel CD3/BCMA Bispecific Antibody Selectively Kills Plasma Cells in Bone Marrow of Healthy Individuals with Improved Safety," (2019) Lupus Science and Medicine 6(Supp 1):Abstract 293.
Nguyen et al., "Functional Heavy-Chain Antibodies in Camelidae," (2001) Advances in Immunology 79:261-296.
Ryan et al., "Antibody Targeting of B-cell Maturation Antigen on Malignant Plasma Cells," (2007) Molecular Cancer Therapeutics 6(11):3009-3018.
Buelow et al., "Development of a fully human T cell engaging bispecfic antibody for the treatment of multiple myeloma," (2017) J Clin OnCol vol. 35 Supplement.
Adams et al., "Prolonged in Vivo Tumour Retention of a Human Diabody Targeting the Extracellular Domain of Human HER2/neu," (1998) British Journal of Cancer 77(9):1405-1412.
Seckinger et al., "Target Expression, Generation, Preclinical Activity, and Pharmacokinetics of the BCMA-T Cell Bispecific Antibody EM801 for Multiple Myeloma Treatment," (2017) Cancer Cell, Cell Press US 31(3):396-410.
Anonymous, "Flow Cytometry Antibody: CD3e Cat. No. CT026-R301, SinoBiological Inc,—Antibody-Catalogue," (2017) Sinobiological, Inc. Retrieved from Internet: URL http://www.sinobiologica.com/flow-cytometry-antibody-elite.html.
Arnett et al., "Crystal Structure of a Human CD3-epsilon/delta Dimer in Complex with a UCHT1 Single-chain Antibody Fragment," (2004) Proc Natl Acad Sci USA 101(46):16268-16273.
Baas et al., "Superhuman Mice," (2014) Science-Business exchange 7(17):1-2.
Borchmann et al., "Phase 1 trial of the Novel Bispecific Molecule H22xKi-4 in Patients with Refractory Hodgkin Lymphoma," (2002) Blood 100(9):3101-3107.
Bruggemann et al., "Heavy-Chain-Only Antibody Expression and B-Cell Development in the Mouse," (2006) Crit. Rev. Immunol. 26(5):377-390.
Christian et al., "Measuring Bacterial Ectoenzyme Activities in Marine Waters Using Mercuric Chloride as a Preservative and Control," (1995) Marine Ecology Progress Series 123:217-224.
Dai et al., "Chimeric Antigen Receptors Modified T-Cells for Cancer Therapy," (2016) J Natl Cancer Inst 108(7):dvj439.
Desmyter et al., "Antigen Specificity and High Affinity Binding Provided by One Single Loop of a Camel Single-domain Antibody," (2001) Journal of Biological Chemistry, American Society for Biochemistry and Molecular Biology 276(28):26285-26290.
Durben et al., "Characterization of a Bispecific FLT3 X CD3 Antibody in an Improved, Recombinant Format for the Treatment of Leukemia," (2015) Molecular Therapy 23(4):648-655.
Gershoni et al., "Epitope Mapping—The First Step in Developing Epitope-based Vaccines," (2007) Biodrugs, Adis International, Ltd. NZ 21(3):145-156.
Hamers-Casterman et al., "Naturally Occurring Antibodies Devoid of Light Chains," (1993) Nature 363:446-448.
Hipp et al., "A Novel BCMA/CD3 Bispecific T-cell Engager for the Treatment of Multiple Myeloma Induces Selective Lysis in Vitro and in Vivo," (2016) 31(8):1743-1751.
Hotzel et al., "A strategy for risk mitigation of antibodies with fast clearance," (2012) mABs 4(6):753-760.
Jackson et al., "Driving CAR T-cells forward," (2016) Nature Reviews Clinical Oncology 13:370-383.
Lindhofer et al., "Preferential Species-restricted Heavy/Light Chain Pairing in Rat/Mouse Quadromas. Implications for a Single-step Purification of Bispecific Antibodies," The Journal of Immunology, 155(1):219-225.

(56) References Cited

OTHER PUBLICATIONS

Link et al., "Anti-CD3-Based Bispecific Antibody Designed for Therapy of Human B-Cell Malignancy can Induce T-cell Activation by Antigen-dependent and Antigen-independent Mechanisms," (1998) Int. J. Cancer 77:251-256.
Mack et al., "A Small Bispecific Antibody Construct Expressed as a Functional Single-chain Molecule with High Tumor Cell Cytotoxicity," (1995) PNAS 92:7021-7025.
Ridgway et al., "'Knobs-into-holes' Engineering of Antibody CH3 Domains for Heavy Chain Heterodimerization," (1996) Protein Engineering 9(7):617-621.
Rossi et al., "Redirected T-cell Killing of Solid Cancers Targeted with an Anti-CD3/Trop-2-Bispecific Antibody is Enhanced in Combination with Interferon-g," 2014 Molecular Cancer Therapeutics 13(10):2341-2351.
Salmeron et al., "A conformational epitope expressed upon association of CD3-epsilon with either CD3-delta or CD3-gamma is the main target for recognition by anti-CD3 monoclonal antibodies." (1991) J. Immunol 147(9):3047-3052.
Trinklein et al., "Abstract LB-090: Sequence-based Discovery of Fully Human Anti-CD3 and Anti-PDL1 Single Domain Antibodies Using Novel Transgenic Rats," (2016) Cancer Research 76(14 Suppl).
Wu et al., "Simultaneous Targeting of Multiple Disease Mediators by a Dual-variable-domain Immunoglobulin," (2007) Nature Biotechnology 25:1290-1297.
Roit, Immunology. Translated from English, Moscow: Mir; 2000.
Hlavacek et al., "Steric Effects on Multivalent Ligand-Receptor Binding: Exclusion of Ligand Sites by Bound Cell Surface Receptors," (1999) Biophysical Journal 76(6):3031-3043.
Plückthun et al., "New protein engineering approaches to multivalent and bispecific antibody fragments," (1997) Immunology 3(2):83-105.
Chothia et al., "Canonical structures for the hypervariable regions of immunoglobulins," (1987) Journal of Molecular Biology 196(4):901-917.
Zhao et al., "A germline knowledge based computational approach for determining antibody complementarity determining regions," (2010) Molecular Immunology 47(4):694-700.
Chothia et al., "Conformations of immunoglobulin hypervariable regions," (1989) Nature 342:877-883.
Honegger, "Yet Another numbering scheme for immunoglobulin variable domains: an automatic modeling and analysis tool," (2001) Journal of Molecular Biology 309(3):657-670.
Ofran et al. "Automated identification of complementarity determining regions (CDRs) reveals peculiar characteristics of CDRs and B cell epitopes." J Immunol. 2008;181:6230-6235.
Almagro "Identification of differences in the specificity-determining residues of antibodies that recognize antigens of different size: implications for the rational design of antibody repertoires." J Mol Recognit. 2004;17: 132-143.
Padlan et al., "Identification of specificity-determining residues in antibodies." (1995) Faseb J. 9:133-139.
Ravetch et al., "Fc Receptors," (1991) Annual Review of Immunology 9:457-492.
Clynes et al., "Fc Receptors are Required in Passie and Active Immunity to Melanoma," (1998) PNAS (USA) 95(2):652-656.
GazzanoSantoro et al., J. Immunol. Methods 202: 163 (1996.
Concepcion et al., "Label-Free Detection of Biomolecular Interactions Using BioLayer Interferometry for Kinetic Characterization," (2009) Combinatorial Chemistry & High Throughput Screening 12(8):791-800.
Langer, "New Methods of Drug Delivery," (1990) Science 249(4976):1527-1533.
Caraccio et al., "Bispecific Antibodies for Multiple Myeloma: A Review of Targets, Drugs, Clinical Trials and Future Directions," (2020) Frontiers in Immunology 11(50):1-25.
Jemal et al., "Cancer Statistics, 2008," ACS Journals (2008) 58(2):71-96.
Waxman et al., "Racial disparities in incidence and outcome in multiple myeloma: a population-based study," (2010) Blood 116(25):5501-5506.
Pulte et al., "Improvement in Survival of Older Adults with Multiple Myeloma: Results of an Updated Period Analysis of SEER Data," (2011) The Oncologist 16(11):1600-1603.
Kumar et al., "Improved survival in multiple myeloma and the impact of novel therapies," (2008) Blood 111(5):2516-2520.
Tueresson et al., "Patterns of Improved Survival in Patients with Multiple Myeloma in the Twenty-First Century: A Population-Based Study," (2010) Journal of Clinical Oncology 28(5):830-834.
Palumbo et al., "Daratumumab, Bortezomib, and Dexamethasone for Multiple Myeloma," (2016) New England Journal of Medicine 375(8):754-766.
Dimopoulos et al., "Daratumumab, Lenalidomide, and Dexamethasone for Multiple Myeloma," (2016) New England Journal of Medicine 375(14):1319-1331.
Mikkilineni et al., "Chimeric antigen receptor T-cell therapies for multiple myeloma," (2017) Blood 130(24):2594-2602.
Pick et al., "Daratumumab resistance is frequent in advanced-stage multiple myeloma patients irrespective of CD38 expression and is related to dismal prognosis," (2018) European Journal of Haematology 100(5):494-501.
Miller et al., "Design, Construction, and In Vitro Analyses of Multivalent Antibodies," (2003) Journal of Immunology 170(9):4854-4861.
Chen et al., "Fusion protein linkers: Property, design and functionality," (2013) Advanced Health Care Materials 65(10):1357-1369.
Kumar et al., "International Myeloma Working Group consensus criteria for response and minimal residual disease assessment in multiple myeloma," (2016) The Lancet Oncology 17(8):e328-e346.
Gust et al., "Endothelial Activation and Blood-Brain Barrier Disruption in Neurotoxicity after Adoptive Immunotherapy with CD19 CAR-T Cells," (2017) Cancer Discovery 7(12):1405-1419.
Giavridis et al., "CAR T cell-induced cytokine release syndrome is mediated by macrophages and abated by IL-1 blockade," (2018) Nature Medicine 24:731-738.
Norelli et al., "Monocyte-derived IL-1 and IL-6 are differentially required for cytokine-release syndrome and neurotoxicity due to CAR T cells," (2018) Nature Medicine 24:739-748.
Anonymous (TeneoBio, Inc.), "A Study of TNB-383B in Subjects with Relapsed or Refractory Multiple Myeloma," (2019) retrieved from the Internet on May 1, 2019 from URL: https://clinicaltrials.gov/ct2/show/NCT03933735, 4 pages.
Buelow et al., "TNB3838.0001: A Multicenter, Phase 1, Open-Label, Dose-Escalation Andexpansion Study of TNB-3838, a Bispecific Antibodytargeting BCMA in Subjects with Relapsed or Refractorymultiple Myeloma," (2019) Blood 134(Supplement 1):1874.
DiLillo et al., "A BCMAxCD3 Bispecifi T Cell-engaging Antibody Demontstrates Robust Antitumor Efficacy Similar to that of Anti-BCMA CAR T Cells," (2020) Blood Advances 5(5):1291-1304.
Rodriguez et al., "Paper: Initial Results of a Phase 1 Study of TNB-383B, a BCMA x CD3 Bispecific T-cell Redirecting Antibody in Relapsed/Refractory Multiple Myeloma," (2020) retrieved from the Internet at URL: https//ash.confex.com/ash/2020/webprogram/Paper139893.html.
Yoon et al., "Both High and Low Avidity Antibodies to the T Cell Receptor can have Agonist Activity," (1994) Immunity 1(7) 563-569.
Kim et al., "Mutational approaches to improve the biophysicalproperties of human single-domain antibodies," (2014) Biochimica Et Biophysica Acta (BBA)—Proteins & Proteomics, Elseviern Netherlands 1844(11):1983-2001.
Chiu et al., "Engineering antibody therapeutics," (2016) Current Opinion in Structural Biology 38:163-173.
Alderson et al., "CAT-8015: A Second-Generation Pseudomonas Exotoxin A—Based Immunotherapy Targeting CD22—Expressing Hematologic Malignancies," (2009) Clinical Cancer Research 15(3):832-839.
"Antibody Therapeutics—Teneobio's Next Generation of Multispecific Antibody Therapeutics," Jan./Feb. 2018, [retrieved on Mar. 21,

(56) References Cited

OTHER PUBLICATIONS

2023]. Retrieved from the Internet <URL: https://drug-dev.com/antibody-therapeutics-teneobios-next-generation-of-multispecific-antibody-therapeutics/>.

Armitage, "A Clinical Evaluation of the International Lymphoma Study Group Classification of Non-Hodgkin's Lymphoma," (1997) Blood, vol. 89(11):3909-3918.

Armour et al., "Recombinant human IgG molecules lacking Fcγ receptor I binding and monocyte triggering activities," (1999) Eur J Immunol. 29(8):2613-2624.

Banihashemi et al., "Development of Specific Nanobodies (VHH) for CD19 Immuno-targeting of Human B-lymphocytes," (2018) Iranian Journal of Basic Medical Sciences 21(5):455-464.

Boesch et al., "Highly parallel characterization of IgG Fc binding interactions," (2014) MAbs 6(4):915-927.

Brudno et al., "T Cells Genetically Modified to Express an Anti-B-Cell Maturation Antigen Chimeric Antigen Receptor Cause Remissions of Poor-Prognosis Relapsed Multiple Myeloma," (2018) J Clin Oncol 36(22):2267-2280.

Bruggemann et al., "Human Antibody Production in Transgenic Animals," (2014) Archivum Immunologiae et Therapie Experimentalis, Birkahaeser Verlag AG 63(2):101-108.

Business Wire: "OMT Therapeutics Announces UniRat TM Alliance with Caltech," May 15, 2015, [Retrieved on May 6, 2020]. Retrieved from the Internet: <URL: https://www.businesswire.com/news/home/20150514006523/en/OMT%20-Therapeutics-Announces-UniRat%20TM%20-%20Alliance-Caltech>.

Canfield et al., "The Binding Affinity of Human IgG for its High Affinity Fc Receptor Is Determined by Multiple Amino Acids in the CH2 Domain and Is Modulated by the Hinge Region," (1991) J Exp Med 173(6):1483-1491.

Chassaing et al., "Dextran Sulfate Sodium (DSS)-Inducted Colitis in Mice," (2014) Current Protocols in Immunology 15(25):1-14.

Chin et al., "The Pharmacology of CD38/NADase: An Emerging Target in Cancer and Diseases of Aging," (2018) Trends in Pharmacological Sciences 39(4):424-436.

Chiu et al., "Hodgkin lymphoma cells express TACI and BCMA receptors and generate survival and proliferation signals in response to BAFF and APRIL," (2007) Blood 109(2):729-739.

Chou et al., "Quantitative Analysis of Dose-Effect Relationships: The Combined Effects of Multiple Drugs or Enzyme Inhibitors," (1984) Hopkins University School of Medicine 22:27-55.

ClinicalTrials.gov, "Study NCT03090659, LCAR-B38M-02 Cells in Treating Relapsed/Refractory (R/R) Multiple Myeloma (LEGEND-2)", Mar. 20, 2017, [retrieved on Sep. 20, 2019], (v1), ID: NCT03090659. Retrieved from the Internet: <URL: <https://clinicaltrials.gov/ct2/history/NCT03090659?V_1=View#StudyPageTop>.

Crescioli et al., "IgG4 Characteristics and Functions in Cancer Immunity," (2016) Curr Allergy Asthma Rep 16:1-11.

Cui et al., "Targeted Integration in Rat and Mouse Embryos with Zinc-finger Nucleases," (2011) Nature Biotechnology 29(1):64-67.

DaSilva, "Abstract 345:A MET × MET Bispecific Antibody that Induces Receptor Degradation Potently Inhibits the Growth of MET-addicted Tumor Xenografts," (2017) AACR Annual Meeting 1-2.

Declaration Nathan D. Trinklein, Ph.D. in EP 2780375 Opposition, EP Application No. 12805432.7.

Declaration of Dr. Rui Zhu, PhD, dated Jun. 9, 2020 in EP 2780375 Opposition, EP Application No. 12805432.7.

Declaration of Kara Olson, dated May 14, 2021 in EP 2780375 Opposition, EP Application No. 12805432.7.

Declaration of Kevin C. Lindquist in EP 2780375 Opposition, EP Application No. 12805432.7.

Dondelinger et al., "Understanding the Significance and Implications of Antibody Numbering and Antigen-binding Surface/Residue Definition," (2018) Frontiers in Immunology 9:1-15.

Duncan et al., "Localization of the binding site for the human high-affinity Fc receptor on IgG ," (1988) Nature 332:563-564.

Force Aldred et al., "Meeting Info: 2018 ASCO-SITC Clinical Immuno-Oncology Symposium, Multispecific Antibodies Targeting CD38 Show Potent Tumor-specific Cytoxicity," (2018) Journal of Clinical Oncology Abstract 36(5):60.

Force Aldred et al., "Winning the Numbers Game: Novel Multi-specific Therapeutics from a Diverse Collection of Human Domain Antibodies," Oct. 10, 2016, [Retrieved on May 6, 2020]. Retrieved from the Internet: <URL: https://2019.lakepharma.com/files/symposiums/Winning%20the%20Numbers%20Game%20-%20Novel%20Multi-specific%20Therapeutics%20from%20a%20Diverse%20Collection%20of%20Human%20Domain%20Antibodies%20-%20Shelley%20Force%20Aldred.pdf> [Inactive Link].

Gupta et al., "Constitutive Inflammatory Cytokine Storm: A Major Threat to Human Health," (2019) Journal of Interferon & Cytokine Research 40(1):19-23.

Haffner et al., "Discovery, Synthesis and Biological Evaluation of Thiazoloquin(az)olin(one)es as Potent CD38 Inhibitors," (2015) Journal of Medical Chemistry 58:3548-3571.

Hamilton et al., "Humanization of Yeast to Produce Complex Terminally Sialylated Glycoproteins," (2006) Science 313(5792):1441-1443.

Hanes et al., "New advances in microsphere-based single-dose vaccines," (1997) Advanced Drug Delivery Reviews 28(1):97-119.

Hermans et al., "The VITAL assay: a versatile fluorometric technique for assessing CTL- and NKT-mediated cytotoxicity against multiple targets in vitro and in vivo," (2004) Journal of Immunological Methods 285(1):25-40.

International Search Report and Written Opinion, dated Oct. 11, 2018, in PCT Application No. PCT/US2018/039917.

Jabbour et al., "Monoclonal Antibodies in Acute Lymphoblastic Leukemia," (2015) Blood 125(26):2010-2016.

Jones, "Analysis of Polypeptides and Proteins," (1993) Advanced Drug Delivery 10(1):29-90.

Kalled et al., "The role of BAFF in immune function and implications for autoimmunity," (2005) Immunol Rev 204:43-54.

Kanda et al., "Establishment of a GDP-mannose 4,6-dehydratase (GMD) knockout host cell line: A new strategy for generating completely non-fucosylated recombinant therapeutics," (2007) Journal of Biotechnology 139:300-310.

Kaneko et al., "Anti-inflammatory Activity of Immunoglobulin G Resulting from Fc Sialylation," (2006) Science 313(5787)670-673.

Kochenderfer et al., "Construction and preclinical evaluation of an anti-CD19 chimeric antigen receptor," (2009) J Immunother 32(7):689-702.

Kohler et al., "Continuous cultures of fused cells secreting antibody of predefined specificity," (1975) Nature 256:495-497.

Laabi et al., "A new gene, BCM, on chromosome 16 is fused to the interleukin 2 gene by a t(4;16)(q26;p13) trans location in a malignant T cell lymphoma," (1992) EMBO J 11(11):3897-3904.

Laabi et al., "The BCMA gene, preferentially expressed during B lymphoid maturation, is bidirectionally transcribed," (1994) Nucleic Acids Res 22(7):1147-1154.

Labrijn et al., "Bispecific Antibodies: A Mechanistic Review of the Pipeline," (2019) Nature Reviews Drug Discovery 18(8):585-608.

Labrijn et al., "Therapeutic IgG4 antibodies engage in Fab-arm exchange with endogenous human IgG4 in vivo," (2009) Nature Biotechnology 27(8):767-771.

Lefranc et al., "The Immunoglobulin FactsBook," (2001) Academic Press, FactsBook Series pp. 1-240.

Lefranc et al., "IMGT, the international ImMunoGeneTics database," (1999) Nucleic Acids Research, 27(1):209-212.

Lund et al., "Expression and characterization of truncated forms of humanized L243 IgG1," (2000) European Journal of Biochemistry 267(24):7246-7256.

Mackay et al., "BAFF and APRIL: a tutorial on B cell survival," (2003) Annu Rev Immunol 21:231-264.

Malik et al., "A Novel Fully Human Bispecific CD19 × CD3 Antibody that Kills Lymphoma Cells with Minimal Cytokine Secretion," (2018) 132(1):1671.

Mariuzza et al., "The Structural Basis of Antigen-antibody Recognition," (1987) Ann Rev Biophys, Biophys Chem 16:139-159.

(56) References Cited

OTHER PUBLICATIONS

Martinez-Cingolani et al., "Development of Chimeric Antigen Receptors for Multiple Myeloma," (2016) Biochem Soc Trans 44(2):397-444.
Menoret et al., "Characterization of Immunoglobulin Heavy Chain Knockout Rats," (2010) European Journal Immunology 40:2932-2941.
Menoret et al., "Transgenic Animals and Genetic Engineering Techniques," (2015) Transgenic Res 24:1079-1085.
Merchant al., "An Efficient Route to Human Bispecific IgG," (1998) Nature Biotechnology, Gale Group, Inc. 16(7):677-681.
Moreaux et al., "BAFF and APRIL protect myeloma cells from apoptosis induced by interleukin 6 deprivation and dexamethasone," (2004) Blood 103(8):3148-3157.
Naddafi et al., "Anti-CD19 Monoclonal Antibodies: A New Approach to Lymphoma Therapy," (2015) IJMCM 4(3):143-151.
Neri et al., "Neutralizing B-cell activating factor antibody improves survival and inhibits osteoclastogenesis in a severe combined immunodeficient human multiple myeloma model" (2007) Clin Cancer Res 13(19):5903-5909.
Ng et al., "B cell-activating factor belonging to the TNF family (BAFF)-R is the principal BAFF receptor facilitating BAFF costimulation of circulating T and B cells," (2004) J Immunol 173(2):807-817.
O'Connor et al., "BCMA Is Essential for the Survival of Long-lived Bone Marrow Plasma Cells," (2004) J Exp Medicine 199(1):91-97.
Omniab: Naturally Optimized Human Antibodies (2016), [Retrieved on May 6, 2020]. Retrieved from the Internet: <URL: http://content.stockpr.com/omniab/db/252/746/file/OmniAb.pdf>.
Presta et al., "Generation of Humanized, High Affinity Anti-tissue Factor Antibody Use as a Novel Antithrombotic Therapeutic," (2001) Thromb Haemost 85:379-389.
Presta et al., "Humanization of an Antibody Directed Against IgE," (1993) Journal of Immunology 151:2623-2632.
Pulte et al., "CD39 Expression on T Lymphocytes Correlates with Severity of Disease in Patients with Chronic Lymphocytic Leukemia," (2011) Clinical Lymphoma, Myeloma & Leukemia 11 (4):367-372.
Raab et al., "Multiple myeloma," (2009) Lancet 374:324-329.
Raje et al., "Anti-BCMA CAR T-Cell Therapy bb2121 in Relapsed or Refractory Multiple Myeloma," (2019) N Engl J Med 380(18):1726-1737.
Rangaswamy et al., "A Novel T-cell Bispecific Antibody Platform for Efficient T-cell Mediated Killing of Tumor Cells with Minimal Cytokine Oncology," (2018) Journal of Clinical Oncology 36(5) Supplement.
Roux et al., "Comparisons of the Ability of Human IgG3 Hinge Mutants, IgM, IgE, and IgA2, to Form Small Immune Complexes: A Role for Flexibility and Geometry," (1998) Journal of Immunology 161(8):4083-4090.
Sadelain et al., "The Basic Principles of Chimeric Antigen Receptor Design," (2013) Cancer Discovery 3(4):388-398.
Sadelain et al., "CD19 CAR T Cells," (2017) Cell 171:1471.
Shallis et al., "The Multi-faceted Potential of CD38 Antibody Targeting in Multiple Myeloma," (2017) Cancer Immunol Immunother 66:697-703.
Shields et al., "High Resolution Mapping of the Binding Site on Human IgG1 for FcγRI, FcγRII, FcγRIII, and FcRn and Design of IgG1 Variants with Improved Binding to the FcγR," (2001) J Biol Chem 276(9):6591-6604.
Shoji-Hosaka et al., "Enhanced Fc-Dependent Cellular Cytotoxicity of Fc Fusion Proteins Derived from TNF Receptor II and LFA-3 by Fucose Removal from Asn-linked Oligosaccharides," (2006) Journal of Biochemistry 140:777-783.
Tao et al., "Structural features of human immunoglobulin G that determine isotype-specific differences in complement activation," (1993) Journal of Experimental Medicine 178(2):661-667.
Thompson et al., "BAFF binds to the tumor necrosis factor receptor-like molecule B cell maturation antigen and is important for maintaining the peripheral B cell population," (2000) J Exp Medicine 192(1):129-135.
Trinklein et al., "Efficient tumor killing and minimal cytokine release with novel T-cell agonist bispecific antibodies," (2019) MABS 11 (4):639-652.
Walker et al., "CD22: An Inhibitory Enigma," (2007) Immunology 123:314-325.
Wang et al., "A systematic approach for analysis and characterization of mispairing in bispecific antibodies with asymmetric architecture," (2018) mAbs 10(8):1226-1235.
Weidle et al., "The Intriguing Options of Multispecific Antibody Formats for Treatment of Cancer," (2013) Cancer Genomics & Proteomics 10(1):1-18.
Werther et al., "Humanization of Anti-lymphocyte Function-associated Antigen (LFA)-1 Monoclonal Antibody and Reengineering of the Humanized Antibody for Binding to Rhesus LFA-1," (1996) Journal of Immunology 157:4986-4995.
Woof et al., "Human antibody-Fc receptor interactions illuminated by crystal structures," (2004) Nat Rev Immunol 4(2):89-99.
Wu et al., "A novel VHH antibody targeting the B cell-activating factor for B-cell lymphoma," International Journal of Molecular Sciences 15(6):9481-9489.
Xianchao, "The expression, purification and activity study of APRIL blocking Qi IJ BCMA-Fc," (2015) Chinese Excellent Doctoral Dissertation Full-text Database (Electronic Journal Network), Issue 2, E059-37:1-26.
Xiaomin et al., "Recent Advances in Tumor Therapy with Chimeric Antigen Receptor Modified T Cells," Medical Review 22(22).
Yan et al., "Recent Advances in Tumor Therapy with Chimeric Antigen Receptor Modified T Cells", Medical Review, (2016), 22(22): 4417-4421.
Rudikoff et al., "Single amino acid substitution altering antigen-binding specificity," (1981) Proc Natl Acad Sci USA 79:1979-1983.

* cited by examiner

| CLONE ID | seq_aa_CDR1 | seq_aa_CDR2 | seq_aa_CDR3 |
|---|---|---|---|
| 316274 | GFTFTNHA (SEQ ID NO: 1) | ISGNGRTT (SEQ ID NO: 4) | AKDGGETLVDS (SEQ ID NO: 8) |
| 316832 | GFTFSSHA (SEQ ID NO: 2) | ISGSGDFT (SEQ ID NO: 5) | AKDEDGGSLLGY (SEQ ID NO: 9) |
| 317693 | GFTFSSHA (SEQ ID NO: 2) | ISGSGDYT (SEQ ID NO: 6) | AKDEDGGSLLGH (SEQ ID NO: 10) |
| 316833 | GFTFSSYA (SEQ ID NO: 3) | ISGSGDYI (SEQ ID NO: 7) | AKEGTGANSSLADY (SEQ ID NO: 11) |

FIG. 1

| CLONE_ID | seq_aa_FR1_FR4 |
|---|---|
| 316274 | QVQLVESGGGLVQPGGSLRLSCAASGFTFTNHAMSWVRQAPGKGLELVSSISGNGRTTYYADSVKGRFTISR DISKNTLDLQMNSLRAEDTAVYYCAKDGGETLVDSRGQGTLVTVSS (SEQ ID NO: 12) |
| 316832 | QVQLVESGGGLVQPGGSLRLSCAASGFTFSSHAMTWVRQAPGKGLEWVAAISGSGDFTHYADSVKGRFTIS RDNSKNTVSLQMNNLRAEDTAVYYCAKDEDGGSLLGYRGQGTLVTVSS (SEQ ID NO: 13) |
| 317693 | EVQLLESGGGLIQPGGSLRLSCAASGFTFSSHAMTWVRQAPGKGLEWVSAISGSGDYTHYADSVKGRFTISR DNSKNTVYLQMNSLRAEDSAVYYCAKDEDGGSLLGHRGQGTLVTVSS (SEQ ID NO: 14) |
| 316833 | EVQLLESGGGLVQPGGSLRLSCAASGFTFSSYAMSWVRQAPGKGLEWVSSISGSGDYIYYADSVKGRFTISRD ISKNTLYLQMNSLRAEDTAVYYCAKEGTGANSSLADYRGQGTLVTVSS (SEQ ID NO: 15) |

FIG. 2

| CLONE_ID | Consensus_seq_nt_FR1_FR4 |
|---|---|
| 316274 | CAGGTGCAGCTGGTGGAGTCTGGGGGAGGCTTGGTACAGCCTGGGGGGTCCCTGAGACTCTCCTGTGCAGCCTCTGGATTCACCTTTAC CAACCATGCCATGAGTTGGGTCCGCCAGGCTCCAGGGAAGGGGCTGGAGTGGTCTCAAGTATTAGTGGTACCACATACTA CGCAGACTCCGTGAAGGGCCGGTTCACCATCTCCAGAGACACATTTCAAGAAACACGCTGGATCTGCAAATGAACAGCCTGAGAGCCGAGG ACACGGGCCGTATATTACTGTGCGAAAGATGGGGGCGAAACTCTAGTTGACTGACTGGGGCCAGGGCACCCTGGTCACCGTCTCCTCA (SEQ ID NO: 16) |
| 316832 | CAGGTGCAGCTGGTGGAGTCTGGGGGAGGCTTGGTACAGCCTGGGGGGTCCCTGAGACTCTCCTGTGCAGCCTCTGGATTCACCTTTAG CAGCCATGCCATGAGCCTGGGTCCGCCAGGCTCCAGGGAAGGGGCTCGAGTGGGTCGCAGTATTAGTGGCAGTGGTCAGACT ACGCAGACTCCGTGAAGGGCCGGTTCACCATCTCCAGAGACAATTCCAAGAACACGGTGTCTCTGCAAATGAACAACCTGAGAGCCGAGG ACACGGCCGTATATTACTGTGCGAAAGATGAGGATGTGGGGAGCTTGCTTGGCTACAGAGGGCACCCTGGTCACCGTCTCCTCA (SEQ ID NO: 17) |
| 317693 | GAGGTGCAGCTGTTGGAGTCTGGGGGAGGCTTGATACAGCCTGGGGGGTCCCTGAGACTCTCCTGTGCAGCCTCTGGATTCACCTTTAG CAGCCATGCCATGACCTGGGTCCGCCAGGCTCCAGGGAAGGGGCTCGAGTGGGTCTCAGTGTCTCAGTTATTAGTGGTAGTGGTATTACACACT ACGCAGACTCCGTGAAGGGTCGGTTCACCATCTCCAGAGACAATTCCAAGAACACGGTGTATCTCCAAATGAACAGTCTGAGAGCCGAGG ACTCGGCCGTATATTACTGTGCGAAAGATGTGGGAGCCTCTGGGGCACAGAGGCCACCCTGGTCACCGTCTCCTCA (SEQ ID NO: 18) |
| 316833 | GAGGTGCAGCTGTTGGAAGTCTGGGGGAGGCTTGGTACAGCCTGGGGGGTCCCTGAGACTCTCCTGTGCAGCCTCTGGATTCACCTTTAG CAGCTATGCCATGAGCTGGGTCCGCCAGGCTCCAGGGAAGGGGCTGGAGTGGGTCTCATCTATTAGTGGTAGTGATTACATATACTA CGCAGACTCCGTGAAGGGCCGGTTCACCATCTCCAGAGACACATCCAAGAACACGCTGTATCTGCAAATGAACAGCCTGAGAGCCGAGGA CACGGCCGTATATTACTGTGCGAAAGAAAGGTACGGTGCCAACAGCAGCTTGGCAGACTACAGAGGCCAGGGCACCCTGGTCACCGTCT CCTCA (SEQ ID NO: 19) |

FIG. 3

| column 1 | column 2 | column 3 | column 4 | column 5 | column 6 | column 7 | column 8 | column 9 | column 10 | column 11 | column 12 | column 13 | | column 14 | |
|---|---|---|---|---|---|---|---|---|---|---|---|---|---|---|---|
| | | | | | | | | 1:100 dilution | 1:100 dilution | | ELISA-Multi-tag | huBCMA | | cyBCMA | |
| | | | | | Conc. | | CHO-cyBCMA | ELISA-hBCMA | ELISA-cyBCMA | ELISA-Lambda | | | | | |
| CLONE_ID | FAMILY_ID | CDR1 | CDR2 | CDR3 | ug/mL | MFI-H929 | | | | | | kdis(1/s) | | kdis(1/s) | |
| 316274 | BCMA_F5 | GFTFTNHA | ISGNGRTT | AKDGGETLVDS | 11.1 | 2276.8 | | 491.6 | 1006.2 | 1.1 | 3.2 | <1.0E-07 | | 9.41E-04 | |
| 316832 | BCMA_F9 | GFTFSSHA | ISGSGDFT | AKDEDGGSLLGY | 10.5 | 2425.1 | | 474.2 | 907.5 | 1.0 | 1.3 | <1.0E-07 | | 1.89E-03 | |
| 317693 | BCMA_F9 | GFTFSSHA | ISGSGDYT | AKDEDGGSLLGH | 3.9 | 1885.0 | 62.9 | 466.3 | 506.9 | 1.2 | 1.6 | | | | |
| 316833 | BCMA_F13 | GFTFSSYA | ISGSGDYI | AKEGTGANSSLADY | 8.8 | 1247.8 | | 466.2 | 949.4 | 0.8 | 0.8 | <1.0E-07 | | 3.22E-04 | |

FIG. 4

SEQUENCE LISTING

```
<160> NUMBER OF SEQ ID NOS: 21

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Thr Asn His Ala
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Phe Thr Phe Ser Ser His Ala
1               5

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3
```

```
Gly Phe Thr Phe Ser Ser Tyr Ala
1               5

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ile Ser Gly Asn Gly Arg Thr Thr
1               5

<210> SEQ ID NO 5
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ile Ser Gly Ser Gly Asp Phe Thr
1               5

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Ser Gly Ser Gly Asp Tyr Thr
1               5

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ile Ser Gly Ser Gly Asp Tyr Ile
1               5

<210> SEQ ID NO 8
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ala Lys Asp Gly Gly Glu Thr Leu Val Asp Ser
1               5                   10
```

<210> SEQ ID NO 9
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 9

```
Ala Lys Asp Glu Asp Gly Gly Ser Leu Leu Gly Tyr
1               5                   10
```

<210> SEQ ID NO 10
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

```
Ala Lys Asp Glu Asp Gly Gly Ser Leu Leu Gly His
1               5                   10
```

<210> SEQ ID NO 11
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 11

```
Ala Lys Glu Gly Thr Gly Ala Asn Ser Ser Leu Ala Asp Tyr
1               5                   10
```

<210> SEQ ID NO 12
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn His
            20                  25                  30

Ala Met Ser Trp Val Arg Gln Ala Pro Gly Lys Gly Leu Glu Leu Val
        35                  40                  45

Ser Ser Ile Ser Gly Asn Gly Arg Thr Thr Tyr Tyr Ala Asp Ser Val
    50                  55                  60

Lys Gly Arg Phe Thr Ile Ser Arg Asp Ile Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Asp Gly Gly Glu Thr Leu Val Asp Ser Arg Gly Gln Gly Thr
            100                 105                 110

Leu Val Thr Val Ser Ser
```

<210> SEQ ID NO 13
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Thr Trp Val Arg Gln Ala Pro Gly Lys Gly Leu Glu Trp Val
        35                  40                  45

Ala Ala Ile Ser Gly Ser Gly Asp Phe Thr His Tyr Ala Asp Ser Val
    50                  55                  60

Lys Gly Arg Phe Thr Ile Ser Arg Asp Asn Ser Lys Asn Thr Val Ser
65                  70                  75                  80

Leu Gln Met Asn Asn Leu Arg Ala Glu Asp Thr Ala Val Tyr Tyr Cys
                85                  90                  95

Ala Lys Asp Glu Asp Gly Gly Ser Leu Leu Gly Tyr Arg Gly Gln Gly
            100                 105                 110

Thr Leu Val Thr Val Ser Ser
        115

<210> SEQ ID NO 14
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ser Ser His
            20                  25                  30

Ala Met Thr Trp Val Arg Gln Ala Pro Gly Lys Gly Leu Glu Trp Val
        35                  40                  45

Ser Ala Ile Ser Gly Ser Gly Asp Tyr Thr His Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Ser Ala Val Tyr Tyr Cys
                85                  90                  95

Ala Lys Asp Glu Asp Gly Gly Ser Leu Leu Gly His Arg Gly Gln Gly
            100                 105                 110

Thr Leu Val Thr Val Ser Ser
        115

<210> SEQ ID NO 15
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Ile Tyr Tyr Ala Asp Ser Val
    50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Thr Gly Ala Asn Ser Ser Leu Ala Asp Tyr Arg Gly
            100                 105                 110

Gln Gly Thr Leu Val Thr Val Ser Ser
        115                 120

<210> SEQ ID NO 16
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
caggtgcagc tggtggagtc tgggggaggc ttggtacagc ctgggggtc cctgagactc      60 tcctgtgcag cctctggatt caccttacc aaccatgcca tgagttgggt ccgccaggct     120
ccagggaagg gctggagtt ggtctcaagt attagtggta atggtcgtac cacatactac     180
gcagactccg tgaagggccg gttcaccatc tccagagaca tttccaagaa cacgctggat     240
ctgcaaatga acagcctgag agccgaggac acggccgtat attactgtgc gaaagatggg     300
ggcgaaactc tagttgactc cagaggccag ggcaccctgg tcaccgtctc ctca           354

<210> SEQ ID NO 17
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
caggtgcagc tggtggagtc tgggggaggc ttggtacagc ctgggggtc cctgagactc      60 tcctgtgcag cctctggatt caccttagc agccatgcca tgacctgggt ccgccaggct     120
ccggggaagg gctggagtg gtcgcagct attagtggag tggtgattt cacacactac     180 gcagactccg tgaagggccg gttcaccatc tccagagaca attccaagaa cacggtgtct     240
ctgcaaatga acaacctgag agccgaggac acggccgtat attactgtgc gaaagatgag     300
gatggtggga gcttgcttgg ctacagaggc cagggcaccc tggtcaccgt ctcctca        357

<210> SEQ ID NO 18
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
gaggtgcagc tgttggagtc tgggggggc ttgatacagc ctggggggtc cctgagactc      60
tcctgtgcag cctctggatt cacctttagc agccatgcca tgacctgggt ccgccaggct    120
ccggggaagg ggctggagtg ggtctcagct attagtggta gtggtgatta cacacactac    180
gcagactccg tgaagggtcg gttcaccatc tccagagaca attccaagaa cacggtgtat    240
ctccaaatga acagtctgag agccgaggac tcggccgtat attactgtgc gaaagatgag    300
gatggtggga gcctcctggg gcacagaggc cagggcaccc tggtcaccgt ctcctca      357
```

<210> SEQ ID NO 19
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19

```
gaggtgcagc tgttggagtc tgggggaggc ttggtacagc ctggggggtc cctgagactc      60
tcctgtgcag cctctggatt cacctttagc agctatgcca tgagctgggt ccgccaggct    120
ccagggaagg ggctggagtg ggtctcatct attagtggta gtggtgatta catatactac    180
gcagactccg tgaagggccg gttcaccatc tccagagaca tatccaagaa cacgctgtat    240
ctgcaaatga acagcctgag agccgaggac acggccgtat attactgtgc gaaagaaggt    300
acgggtgcca acagcagctt ggcagactac agaggccagg gcaccctggt caccgtctcc    360
tca                                                                    363
```

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (5)..(5)
<223> OTHER INFORMATION: /replace="Thr"
<220> FEATURE:
<221> NAME/KEY: VARIANT
<222> LOCATION: (6)..(6)
<223> OTHER INFORMATION: /replace="Asn"
<220> FEATURE:
<221> NAME/KEY: VARIANT
<222> LOCATION: (7)..(7)
<223> OTHER INFORMATION: /replace="Tyr"
<220> FEATURE:
<221> NAME/KEY: SITE
<222> LOCATION: (1)..(8)
<223> OTHER INFORMATION: /note="Variant residues given in the sequence have no preference with respect to those in the annotations for variant positions"

<400> SEQUENCE: 20

```
Gly Phe Thr Phe Ser Ser His Ala
1               5

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Asn"
<220> FEATURE:
<221> NAME/KEY: VARIANT
<222> LOCATION: (6)..(6)
<223> OTHER INFORMATION: /replace="Arg"
<220> FEATURE:
<221> NAME/KEY: VARIANT
<222> LOCATION: (7)..(7)
<223> OTHER INFORMATION: /replace="Phe" or "Tyr"
<220> FEATURE:
<221> NAME/KEY: VARIANT
<222> LOCATION: (8)..(8)
<223> OTHER INFORMATION: /replace="Ile"
<220> FEATURE:
<221> NAME/KEY: SITE
<222> LOCATION: (1)..(8)
<223> OTHER INFORMATION: /note="Variant residues given in the sequence
      have no preference with respect to those in the annotations for
      variant positions"

<400> SEQUENCE: 21

Ile Ser Gly Ser Gly Asp Thr Thr
1               5
```

ANTI-BCMA HEAVY CHAIN-ONLY ANTIBODIES

CROSS REFERENCE TO RELATED APPLICATIONS

This application claims priority benefit of the filing date of U.S. Provisional Patent Application Ser. No. 62/522,355, filed on Jun. 20, 2017, the disclosure of which application is herein incorporated by reference in its entirety.

FIELD OF THE INVENTION

The present invention concerns anti-BCMA heavy chain-only antibodies (UniAb). The invention further concerns methods of making such antibodies, compositions, including pharmaceutical compositions, comprising such antibodies, and their use to treat a B-cell disorder characterized by the expression of BCMA.

BACKGROUND OF THE INVENTION

B-Cell Maturation Antigen (BCMA)

BCMA, also known as tumor necrosis factor superfamily member 17 (TNFRSF17) (UniProt Q02223), is a cell surface receptor exclusively expressed on plasma cells and plasmablasts. BCMA is a receptor for two ligands in the tumor necrosis factor (TNF) superfamily: APRIL (a proliferation-inducing ligand, also known as TNFSF13; TALL-2 and TRDL-1; the high affinity ligand for BCMA) and B cell activation factor (BAFF) (also known as BLyS; TALL-1; THANK; zTNF4; TNFSF20; and D8Ertd387e; the low affinity ligand for BCMA). APRIL and BAFF are growth factors that bind BCMA and promote survival of plasma cells. BCMA is also highly expressed on malignant plasma cells in human multiple myeloma (MM). Antibodies binding to BCMA are described, for example, in Gras et al., 1995, *Int. Immunol.* 7:1093-1106, WO200124811 and WO200124812. Anti-BCMA antibodies that cross-react with TACI are described in WO2002/066516. Bispecific antibodies against BCMA and CD3 are described, for example, in US 2013/0156769 A1 and US 2015/0376287 A1. An anti-BCMA antibody-MMAE or -MMAF conjugate has been reported to selectively induce killing of multiple myeloma cells (Tai et al., *Blood* 2014, 123(20): 3128-38). Ali et al., *Blood* 2016, 128(13):1688-700, have reported that in a clinical trial (#NCT02215967) chimeric antigen receptor (CAR) T cells targeting BCMA resulted in remission of multiple myeloma in human patients.

Heavy Chain-Only Antibodies

In a conventional IgG antibody, the association of the heavy chain and light chain is due in part to a hydrophobic interaction between the light chain constant region and the CH1 constant domain of the heavy chain. There are additional residues in the heavy chain framework 2 (FR2) and framework 4 (FR4) regions that also contribute to this hydrophobic interaction between the heavy and light chains.

It is known, however, that sera of camelids (sub-order Tylopoda which includes camels, dromedaries and llamas) contain a major type of antibodies composed solely of paired H-chains (heavy-chain only antibodies or UniAbs). The UniAbs of Camelidae (*Camelus dromedarius, Camelus bactrianus, Lama glama, Lama guanaco, Lama alpaca* and *Lama vicugna*) have a unique structure consisting of a single variable domain (VHH), a hinge region and two constant domains (CH2 and CH3), which are highly homologous to the CH2 and CH3 domains of classical antibodies. These UniAbs lack the first domain of the constant region (CH1) which is present in the genome, but is spliced out during mRNA processing. The absence of the CH1 domain explains the absence of the light chain in the UniAbs, since this domain is the anchoring place for the constant domain of the light chain. Such UniAbs naturally evolved to confer antigen-binding specificity and high affinity by three CDRs from conventional antibodies or fragments thereof (Muyldermans, 2001; J Biotechnol 74:277-302; Revets et al., 2005; Expert Opin Biol Ther 5:111-124). Cartilaginous fish, such as sharks, have also evolved a distinctive type of immunoglobulin, designated as IgNAR, which lacks the light polypeptide chains and is composed entirely by heavy chains. IgNAR molecules can be manipulated by molecular engineering to produce the variable domain of a single heavy chain polypeptide (vNARs) (Nuttall et al. Eur. J. Biochem. 270, 3543-3554 (2003); Nuttall et al. Function and Bioinformatics 55, 187-197 (2004); Dooley et al., Molecular Immunology 40, 25-33 (2003)).

The ability of heavy chain-only antibodies devoid of light chain to bind antigen was established in the 1960s (Jaton et al. (1968) Biochemistry, 7, 4185-4195). Heavy chain immunoglobulin physically separated from light chain retained 80% of antigen-binding activity relative to the tetrameric antibody. Sitia et al. (1990) Cell, 60, 781-790 demonstrated that removal of the CH1 domain from a rearranged mouse μ gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. Biochim. Biophys. Acta. 1431, 37-46 (1999)) and the VHH portion can be readily cloned and expressed in yeast (Frenken, L. G. J., et al. J. Biotechnol. 78, 11-21 (2000)). Their levels of expression, solubility and stability are significantly higher than those of classical F(ab) or Fv fragments (Ghahroudi, M. A. et al. FEBS Lett. 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, Immunology; 109(1), 93-101; Brüggemann et al., Crit. Rev. Immunol.; 2006, 26(5):377-90; and Zou et al., 2007, J Exp Med; 204(13): 3271-3283. The production of knockout rats via embryo microinjections of zinc-finger nucleases is described in Geurts et al., 2009, Science, 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domain are described, for example, in Iri-Sofia et al., 2011, Experimental Cell Research 317:2630-2641 and Jamnani et al., 2014, Biochim Biophys Acta, 1840:378-386.

SUMMARY OF THE INVENTION

The present invention concerns heavy chain-only antibodies binding to human B-Cell Maturation Antigen (BCMA).

In one aspect, the invention concerns heavy chain-only anti-BCMA antibodies comprising a heavy chain variable region comprising:
(a) a CDR1 having two or fewer substitutions in any of the amino acid sequences of SEQ ID NO:1, 2, or 3; and/or
(b) a CDR2 having two or fewer substitutions in any of the amino acid sequences of SEQ ID NOs: 4 to 7; and/or
(c) a CDR3 having two or fewer substitutions in any of the amino acid sequences of SEQ ID NOs:8 to 11.

In one embodiment, the CDR1, CDR2, and CDR3 sequences are present in a human framework.

In another embodiment, the heavy chain-only anti-BCMA antibodies further comprise a heavy chain constant region sequence in the absence of a CH1 sequence.

In yet another embodiment, the heavy chain-only anti-BCMA antibody comprises:
(a) a CDR1 sequence selected from the group consisting of SEQ ID NOs: 1 to 3; and/or
(b) a CDR2 sequence selected from the group consisting of SEQ ID NOs: 4 to 7; and/or
(c) a CDR3 sequence selected from the group consisting of SEQ ID NOs: 8 to 11.

In a further embodiment, the heavy chain-only antibody comprises:
(a) a CDR1 sequence selected from the group consisting of SEQ ID NOs: 1 to 3; and
(b) a CDR2 sequence selected from the group consisting of SEQ ID NOs: 4 to 7; and
(c) a CDR3 sequence selected from the group consisting of SEQ ID NOs:8 to 11.

In a still further embodiment, the heavy chain only antibody comprises
(i) a CDR1 sequence of SEQ ID NO: 1, a CDR2 sequence of SEQ ID NO: 4, and a CDR3 sequence of SEQ ID NO: 8; or
(ii) a CDR1 sequence of SEQ ID NO: 2, a CDR2 sequence of SEQ ID NO: 5, and a CDR3 sequence of SEQ ID NO: 9; or
(iii) a CDR1 sequence of SEQ ID NO: 2, a CDR2 sequence of SEQ ID NO: 6, and a CDR3 sequence of SEQ ID NO: 10; or
(iv) a CDR1 sequence of SEQ ID NO: 3, a CDR2 sequence of SEQ ID NO: 7, and a CDR3 sequence of SEQ ID NO: 11.

In another embodiment, the heavy chain-only anti-BCMA antibody comprises a heavy chain variable region having at least 95% sequence identity to any of the sequences of SEQ ID NOs: 12 to 15.

In a further embodiment, the heavy chain-only anti-BCMA antibody comprises a heavy chain variable region sequence selected from the group consisting of SEQ ID NOs: 12 to 15.

In a further aspect, the invention concerns a heavy chain-only anti-BCMA antibody comprising a heavy chain variable region comprising a heavy chain variable comprising
(a) a CDR1 sequence of the formula

G F T F X1 X2 X3 A where
X1 is S or T;
X2 is S or N;
X3 is H or Y, or (b) a CDR2 sequence of the formula

I S G X4 G X5 D6 X7 where
X4 is S or N;
X5 is D or R;
X6 is T, F or Y; or
X7 is T or I,
(c) a CDR3 sequence selected from the group consisting of AKDGGETLVDS (SEQ ID NO: 8), AKDEDGGSLLGY (SEQ ID NO: 9), AKDEDGGSLLGH (SEQ ID NO: 10), and AKEGTGANSSLADY (SEQ ID NO: 11).

In another aspect, the invention concerns a heavy chain-only antibody binding to human B-Cell Maturation Antigen (BCMA) comprising a heavy chain variable region comprising CDR1, CDR2 and CDR3 sequences in a human VH framework wherein the CDR sequences have 2 or fewer amino acid substitutions in a CDR sequence selected from the group consisting of SEQ ID NOs:1-11.

In one embodiment, the anti-BCMA heavy chain-only antibody comprises a heavy chain variable region comprising CDR1, CDR2 and CDR3 sequences in a human VH framework wherein the CDR sequences are selected from the group consisting of SEQ ID NOs:1-11.

In another embodiment, the invention concerns an anti-BCMA heavy chain-only antibody comprising a heavy chain variable region comprising
(i) a CDR1 sequence of SEQ ID NO: 1, a CDR2 sequence of SEQ ID NO: 4, and a CDR3 sequence of SEQ ID NO: 8; or
(ii) a CDR1 sequence of SEQ ID NO: 2, a CDR2 sequence of SEQ ID NO: 5, and a CDR3 sequence of SEQ ID NO: 9; or
(iii) a CDR1 sequence of SEQ ID NO: 2, a CDR2 sequence of SEQ ID NO: 6, and a CDR3 sequence of SEQ ID NO: 10; or
(iv) a CDR1 sequence of SEQ ID NO: 3, a CDR2 sequence of SEQ ID NO: 7, and a CDR3 sequence of SEQ ID NO: 11,
in a human VH framework.

In all aspects and embodiments, the heavy chain-only antibodies may be multi-specific, such as bispecific, and may, for example, bind to two different BCMA proteins or two different epitopes on the same BCMA protein.

In one embodiment, the heavy chain-only antibody has binding affinity to an effector cell.

In a second embodiment, the heavy chain-only antibody has binding affinity to a T-cell antigen, such as CD3.

In a third embodiment, the heavy chain-only antibody is in a CAR-T format.

In another aspect, the invention concerns a pharmaceutical composition comprising a heavy chain-only antibody as hereinabove described.

In yet another aspect, the invention concerns a method for the treatment of a B-cell disorder characterized by the expression of BCMA, the method comprising administering to a subject with said disorder a heavy chain-only antibody, or a pharmaceutical composition, as hereinabove described.

In one embodiment, the B-cell disorder is multiple myeloma (MM).

In another embodiment, the B-cell disorder is systemic lupus erythematosus (SLE).

In a further aspect, the invention concerns a polynucleotide encoding an anti-BCMA heavy chain-only antibody as described herein.

In a still further aspect, the invention concerns a vector comprising a polynucleotide encoding an anti-BCMA heavy chain-only antibody as described herein.

In another aspect, the invention concerns a cell comprising a polynucleotide encoding an anti-BCMA heavy chain-only antibody as described herein, or a vector comprising such polynucleotide.

In yet another aspect, the invention concerns a method of producing an anti-BCMA heavy chain-only antibody as described herein, the method comprising growing a cell comprising a polynucleotide encoding an anti-BCMA heavy chain-only antibody as described herein, or a vector comprising such polynucleotide, under conditions permissive for expression of the protein, and isolating the antibody from the cell and/or the cell culture medium.

In a further aspect, the invention concerns a method of making an anti-BCMA heavy chain-only antibody as described herein, the method comprising immunizing a UniRat animal with BCMA and identifying BCMA-binding heavy chain sequences.

These and further aspect will be further explained in the rest of the disclosure, including the Examples.

BRIEF DESCRIPTION OF THE DRAWINGS

FIG. 1 shows the CDR1, CDR2 and CDR3 amino acid sequences of 4 heavy chain-only anti-BCMA antibodies of the invention.

FIG. 2 shows the heavy chain variable region amino acid sequences of 4 heavy chain-only anti-BCMA antibodies of the invention.

FIG. 3 shows the nucleic acid sequence encoding the heavy chain variable region sequences of 4 heavy chain-only anti-BCMA antibodies of the invention.

FIG. 4 shows binding to BCMA protein and BCMA-expressing cell lines of 4 heavy-chain antibodies. Column 1 indicates the clone ID of the HCAb. Column 2 indicates the family ID of the HCAb based on the CDR3 sequence. Column 3 indicates the CDR1 amino acid sequence. Column 4 indicates the CDR2 amino acid sequence. Column 5 indicates the CDR3 amino acid sequence. Column 6 indicates the concentration of the expressed HCAb in ug/mL. Column 7 indicates the mean fluorescent intensity of cell binding to H929 human cells that express BCMA. Column 8 indicates the mean fluorescent intensity of cell binding to CHO cells that express cyno BCMA. Column 9 indicates the ELISA fold over background signal of human BCMA protein binding. Column 10 indicates the ELISA fold over background signal of cyno BCMA protein binding. Column 11 indicates the ELISA fold over background signal of lambda protein binding, an off-target control. Column 12 indicates the ELISA fold over background signal of a multi-tag protein binding, an off-target control. Column 13 indicates the binding off-rate to human BCMA protein measured by the Octet. Column 14 indicates the binding off-rate to cyno BCMA protein measured by the Octet.

DETAILED DESCRIPTION OF THE PREFERRED EMBODIMENTS

Figure 5:
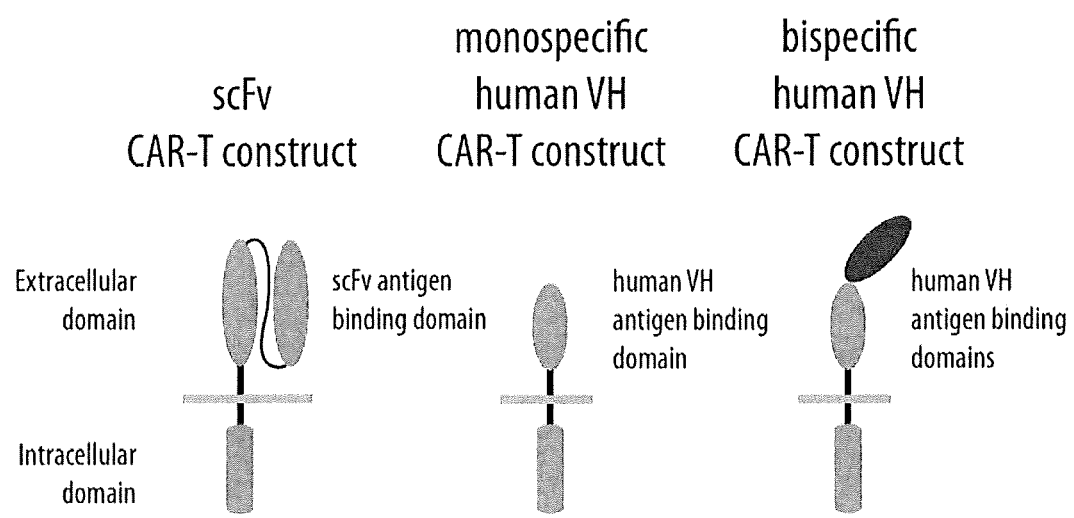
FIG. 5 is a graphic illustration of an scFv CAR-T construct, a monospecific human VH CAR-T construct, and a bispecific human VH CAR-T construct.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

I. Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The terms "heavy chain-only antibody," "heavy-chain antibody" and "UniAb" are used interchangeably, and refer, in the broadest sense, to antibodies lacking the light chain of a conventional antibody. Since the homodimeric UniAbs lack a light chain and thus a VL domain, the antigen is recognized by one single domain, i.e., the variable domain of the heavy chain of a heavy-chain antibody (VH). The term specifically includes, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (sUniDabs). In one embodiment, the heavy chain-only antibody is composed of the variable region antigen-binding domain composed of framework 1, CDR1, framework 2, CDR2, framework 3, CDR3, and framework 4. In one embodiment, the heavy chain-only antibody is composed of an antigen-binding domain, at least part of a hinge region and CH2 and CH3 domains. In another embodiment, the heavy chain-only antibody is composed of an antigen-binding domain, at least part of a hinge region and a CH2 domain. In a further embodiment, the heavy chain-only antibody is composed of an antigen-binding domain, at least part of a hinge region and a CH3 domain. Heavy chain-only antibodies in which the CH2 and/or CH3 domain is truncated are also included herein. In a further embodiment the heavy chain is composed of an antigen binding domain, and at least one CH (CH1, CH2, CH3, or CH4) domain but no hinge region. The heavy chain-only antibody can be in the form of a dimer, in which two heavy chains are disulfide bonded other otherwise, covalently or non-covalently attached with each other. The heavy chain-only antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular IgG1 subtype. In one embodiment, the heavy chain-only antibodies herein are used as a binding (targeting) domain of a chimeric antigen receptor (CAR).

The term "BCMA" as used herein relates to human B cell maturation antigen, also known as BCMA, CD269, and TNFRSF17 (UniProt Q02223), which is a member of the tumor necrosis receptor superfamily that is preferentially expressed in differentiated plasma cells. The extracellular domain of human BCMA consists, according to UniProt of amino acids 1-54 (or 5-51).

The terms "anti-BCMA heavy chain-only antibody" and "BCMA heavy chain-only antibody" are used herein to refer to a heavy chain-only antibody as hereinabove defined, immunospecifically binding to BCMA.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" residues 26-32 (H1), 53-55 (H2) and 96-101 (H3) in the heavy chain variable domain; Chothia and Lesk J. Mol. Biol. 196:901-917 (1987)). "Framework Region" or "FR" residues are those variable domain residues other than the hypervariable region residues as herein defined.

Exemplary CDR designations are shown herein, however one of skill in the art will understand that a number of definitions of the CDRs are commonly in use, including the Kabat definition (see "Zhao et al. A germline knowledge based computational approach for determining antibody complementarity determining regions." Mol Immunol. 2010; 47:694-700), which is based on sequence variability and is the most commonly used. The Chothia definition is based on the location of the structural loop regions (Chothia et al. "Conformations of immunoglobulin hypervariable regions." Nature. 1989; 342:877-883). Alternative CDR definitions of interest include, without limitation, those disclosed by Honegger, "Yet another numbering scheme for immunoglobulin variable domains: an automatic modeling and analysis tool." J Mol Biol. 2001; 309:657-670; Ofran et al. "Automated identification of complementarity determining regions (CDRs) reveals peculiar characteristics of CDRs and B cell epitopes." J Immunol. 2008; 181:6230-6235; Almagro "Identification of differences in the specificity-determining residues of antibodies that recognize antigens of different size: implications for the rational design of antibody repertoires." J Mol Recognit. 2004; 17:132-143; and Padlan et al. "Identification of specificity-determining residues in antibodies." Faseb J. 1995; 9:133-139., each of which is herein specifically incorporated by reference.

The term "2 (two) or fewer substitutions" in an amino acid sequence is used herein to mean 2 (two), 1 (one) or 0 (zero) substitutions in the reference amino acid sequence.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. "Multi-specific" antibodies specifically include antibodies comprising a combination of different binding entities as well as antibodies comprising more than one of the same binding entity. The terms "multi-specific antibody," multi-specific single chain-only antibody" and "multi-specific UniAb" are used herein in the broadest sense and cover all antibodies with more than one binding specificity.

The term "valent" as used herein refers to a specified number of binding sites in an antibody molecule.

A "multi-valent" antibody has two or more binding sites. Thus, the terms "bivalent", "trivalent", and "tetravalent" refers to the presence of two binding sites, three binding sites, and four binding sites, respectively. Thus, a bispecific antibody according to the invention is at least bivalent and may be trivalent, tetravalent, or otherwise multi-valent.

A large variety of methods and protein configurations are known and used for the preparation of bispecific monoclonal antibodies (BsMAB), tri-specific antibodies, and the like.

The term "bispecific three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy chain only antibody comprising an Fc portion comprising CH2 and/or CH3 and/or CH4 domains, in the absence of a CH1 domain, and an antigen binding domain that binds an epitope of a second antigen or a different epitope of the first antigen, where such binding domain is derived from or has sequence identity with the variable region of an antibody heavy or light chain. Parts of such variable region may be encoded by VH and/or VL gene segments, D and JH gene segments, or JL gene segments. The variable region may be encoded by rearranged VHDJH, VLDJH, VHJL, or VLJL gene segments. A TCA protein makes use of a heavy chain-only antibody as hereinabove defined.

The term "chimeric antigen receptor" or "CAR" is used herein in the broadest sense to refer to an engineered receptor, which grafts a desired binding specificity (e.g., the antigen-binding region of a monoclonal antibody or other ligand) to membrane-spanning and intracellular-signaling domains. Typically, the receptor is used to graft the specificity of a monoclonal antibody onto a T cell to create a chimeric antigen receptors (CAR). (J Natl Cancer Inst, 2015; 108(7):dvj439; and Jackson et al., Nature Reviews Clinical Oncology, 2016; 13:370-383.) Representative monospecific and bispecific CAR-T constructs comprising a human VH extracellular binding domain are shown in FIG. 5, in comparison to an scFv CAR-T construct.

By "human idiotype" is meant a polypeptide sequence epitope present on a human antibody in the immunoglobulin heavy and/or light chain variable region. The term "human idiotype" as used herein includes both naturally occurring sequences of a human antibody, as well as synthetic sequences substantially identical to the polypeptide found in naturally occurring human antibodies. By "substantially" is meant that the degree of amino acid sequence identity is at least about 85%-95%. Preferably, the degree of amino acid sequence identity is greater than 90%, more preferably greater than 95%.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g., from blood or PBMCs as described herein.

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., J. Immunol. Methods 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, Calif.) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., Comb Chem High Throughput Screen, 12(8), 791-800, 2009).

An "epitope" is the site on the surface of an antigen molecule to which a single antibody molecule binds. Generally an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s).

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g., mouse, rat, etc.

The term "CD3" refers to the human CD3 protein multi-subunit complex. The CD3 protein multi-subunit complex is composed to 6 distinctive polypeptide chains. These include a CD3γ chain (SwissProt P09693), a CD3δ chain (SwissProtP04234), two CD3e chains (SwissProt P07766), and one CD3ζ chain homodimer (SwissProt 20963), and which is associated with the T cell receptor a and β chain. The term "CD3" includes any CD3 variant, isoform and species homolog which is naturally expressed by cells (including T cells) or can be expressed on cells transfected with genes or cDNA encoding those polypeptides, unless noted.

A "BCMA×CD3 antibody" is a multispecific heavy chain-only antibody, such as a bispecific heavy chain-only antibody, which comprises two different antigen-binding regions, one of which binds specifically to the antigen BCMA and one of which binds specifically to CD3.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0° C.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301. Vincent Lee Ed., Marcel Dekker, Inc., New York, N.Y., Pubs. (1991) and Jones. A. Adv. Drug Delivery Rev. 10: 29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomeriation), clipping/hydrolysis/fragmentation (e.g., hinge region fragmentation), succinimide formation, unpaired cysteine(s), N-terminal extension, C-terminal processing, glycosylation differences, etc.

II. Detailed Description

Anti-BCMA Antibodies

The present invention provides heavy chain-only antibodies (UniAbs) that bind to human BCMA. The anti-BCMA UniAbs of the invention comprise a set of CDR sequences as defined herein and shown in FIG. 1, and are exemplified by the provided heavy chain variable region (VH) sequences of SEQ ID NOs 12 to 15, set forth in FIG. 2, encoded by the nucleic acid sequences of SEQ ID NOs: 16-19, set forth in FIG. 3. These antibodies provide a number of benefits that contribute to utility as clinically therapeutic agent(s). The antibodies include members with a range of binding affinities, allowing the selection of a specific sequence with a desired binding affinity.

A suitable antibody may be selected from those provided herein for development and therapeutic or other use, including, without limitation, use as a bispecific or tri-specific antibody, or part of a CAR-T structure, e.g., as shown in FIG. 5.

Determination of affinity for a candidate protein can be performed using methods known in the art, such as Biacore measurements. Members of the antibody family may have an affinity for BCMA with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., blocking, a BCMA biological activity, including in vitro assays, pre-clinical models, and clinical trials, as well as assessment of potential toxicity.

Members of the antibody family herein are not cross-reactive with the BCMA protein of Cynomolgus macaque, but can be engineered to provide cross-reactivity with the BCMA protein of Cynomolgus macaque, or with the BCMA of any other animal species, if desired.

In some embodiments, the anti-BCMA UniAb antibodies herein comprise a VH domain, comprising CDR1, CDR2 and CDR3 sequences in a human VH framework. The CDR sequences may be situated, as an example, in the region of around amino acid residues 26-35; 53-59; and 98-117 for CDR1, CDR2 and CDR3, respectively, of the provided exemplary variable region sequences set forth in SEQ ID NOs: 16 to 50. It will be understood by one of skill in the art that the CDR sequences may be in different positions if a different framework sequence is selected, although generally the order of the sequences will remain the same.

The CDR1 and CDR2 sequences of the anti-BCMA antibodies of the present invention may be encompassed by the following structural formulas, where an X indicates a variable amino acid, which may be specific amino acids as indicated below.

```
CDR1
G T F F X1 X2 X3 A
``` where
X1 is S or T;
X2 is S or N;
X3 is H or Y.

In one embodiment, both X1 and X2 are S. In another embodiment, X3 is H. In a further embodiment, X1 X2 X3 has the sequence SSH. In other embodiments, CDR1 comprises the sequence GFTFSSHA (SEQ ID NO: 2) or the sequence GFTFSSYA (SEQ ID NO: 3) or the sequence of GFTFTNHA (SEQ ID NO: 1).

```
CDR2
I S G X4 G X5 D6 X7
``` where
X4 is S or N;
X5 is D or R;
X6 is T, F or Y; and
X7 is T or I.

In one embodiment, X4 is S. In another embodiment, X5 is D. In a further embodiment, X4 is S and X5 is D. In a still further embodiment, X6 is Y. In another embodiment, X4 is S, X5 is D and X6 is Y. In yet another embodiment, X7 is T. In a further embodiment, X4 is S, X5 is D and X7 is T. In other embodiments, CDR2 comprise the sequence of SEQ ID NO: 4, or SEQ ID NO: 5, or SEQ ID NO: 6, or SEQ ID NO: 7.

In one embodiment, CDR3 is selected from the group consisting of AKDGGETLVDS (SEQ ID NO: 8), AKDEDGGSLLGY (SEQ ID NO: 9), AKDEDGGSLLGH (SEQ ID NO: 10), and AKEGTGANSSLADY (SEQ ID NO: 11).

Representative CDR1, CDR2, and CDR3 sequences are shown in FIG. 1.

In one embodiment, the anti-BCMA heavy chain-only antibody of the present invention comprises the CDR1 sequence of SEQ ID NO: 1; the CDR2 sequence of SEQ ID NO: 4 and a CDR3 sequence of SEQ ID NO: 8.

In another embodiment, the anti-BCMA heavy chain-only antibody of the present invention comprises the CDR1 sequence of SEQ ID NO: 2; a CDR2 sequence of SEQ ID NO: 5; and a CDR3 sequence of SEQ ID NO: 9.

In a further embodiment, the anti-BCMA heavy chain-only antibody of the present invention comprises the CDR1 sequence of SEQ ID NO:2; the CDR2 sequence of SEQ ID NO: 6; and the CDR3 sequence of SEQ ID NO: 10.

In a still further embodiment, the anti-BCMA heavy chain-only antibody of the present invention comprises the CDR1 sequence of SEQ ID NO: 3, the CDR2 sequence of SEQ ID NO: 7, and the CDR3 sequence of SEQ ID NO: 11.

In further embodiments, the anti-BCMA antibody of the present invention comprises any of the heavy chain variable region amino acid sequences of SEQ ID NOs: 12 to 15 (FIG. 2).

In some embodiments, a CDR sequence in the anti-BMA antibodies of the present invention comprises two or fewer amino acid substitutions relative to a CDR1, CDR2 and/or CDR3 sequence or set of CDR1, CDR2 and CDR3 sequences in any one of SEQ ID NOs:1 to 11 (FIG. 1). In some embodiments, said amino acid substitution(s) are one or two of amino acid positions 5-7 of CDR1, and/or one or two of the amino acid positions 4, 6, 8 of CDR2, and/or one or two amino acid positions of CDR3, relative to the formulas and sequences provided above. In some embodiments, the heavy chain-only anti-BCMA antibodies herein will comprise a heavy chain variable region sequence with at least 85% identity, at least 90% identity, at least 95% identity, at least 98% identify, or at least 99% identity to any of the heavy chain variable region sequences shown in FIG. 2 (SEQ ID NOs: 12-15).

In some embodiments, bispecific or multispecific antibodies are provided, which may have any of the configurations discussed herein, including, without limitation, a three chain bispecific antibody. Bispecific antibodies comprise at least the heavy chain variable region of an antibody specific for a protein other than BCMA.

Where a protein of the invention is a bispecific antibody, one binding moiety is specific for human BCMA while the other arm may be specific for target cells, tumor associated antigens, targeting antigens, e.g., integrins, etc., pathogen antigens, checkpoint proteins, and the like. Target cells specifically include cancer cells, such as hematologic tumors, e.g., B-cell tumors, as discussed below.

Various formats of bispecific antibodies are within the ambit of the invention, including, without limitation, single chain polypeptides, two chain polypeptides, three chain polypeptides, four chain polypeptides, and multiples thereof. The bispecific antibodies herein specifically include T-cell bispecific antibodies binding to BCMA, which is selectively expressed on plasma cells (PCs) and multiple myeloma (MM), and CD3 (anti-BCMA×anti-CD3 antibodies). Such antibodies induce potent T-cell mediated killing of cells carrying BCMA, and can be used to treat tumors, in particular hematologic tumors, such as B-cell tumors, as discussed below.

Bispecific antibodies against CD3 and BCMA are described, for example, in WO2007117600, WO2009132058, WO2012066058, WO2012143498, WO2013072406, WO2013072415, and WO2014122144, and in US 20170051068.

Pharmaceutical Compositions

It is another aspect of the present invention to provide pharmaceutical compositions comprising one or more antibodies of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

Pharmaceutical composition of the antibodies used in accordance with the present invention are prepared for storage by mixing proteins having the desired degree of purity with optional pharmaceutically acceptable carriers, excipients or stabilizers (see, e.g., Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, preferably in physiologically-compatible buffers to reduce discomfort at the site of injection. The solution can contain carriers, excipients, or stabilizers as discussed above. Alternatively, antibodies can be in lyophilized form for constitution with a suitable vehicle, e.g., sterile pyrogen-free water, before use.

Anti-BCMA antibody formulations are disclosed, for example, in U.S. Pat. No. 9,034,324. Similar formulations can be used for the proteins of the present invention. Subcutaneous antibody formulations are described, for example, in US 20160355591 and US 20160166689.

Methods of Use

The pharmaceutical compositions herein can be used for the treatment of B-cell related disorders, including B-cell and plasma cell malignancies and autoimmune disorders characterized by the expression or overexpression of BCMA.

Such B-cell related disorders include B-cell and plasma cell malignancies and autoimmune disorders, including, without limitation, plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, small lymphocytic lymphoma, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy.

The plasma cell disorders characterized by the expression of BCMA include Multiple Myeloma (MM). MM is a B-cell malignancy characterized by a monoclonal expansion and accumulation of abnormal plasma cells in the bone marrow compartment. Current therapies for MM often cause remissions, but nearly all patients eventually relapse and die. There is substantial evidence of an immune-mediated elimination of myeloma cells in the setting of allogeneic hematopoietic stem cell transplantation; however, the toxicity of this approach is high, and few patients are cured. Although some monoclonal antibodies have shown promise for treating MM in preclinical studies and early clinical trials, consistent clinical efficacy of any monoclonal antibody therapy for MM has not been conclusively demonstrated. There is therefore a great need for new therapies, including immunotherapies, for MM (see, e.g. Carpenter et al., Clin Cancer Res 2013, 19(8):2048-2060).

Overexpression or activation of BCMA by its proliferation-inducing ligand, APRIL it known to promote human Multiple Myeloma (MM) progression in vivo. BCMA has also been shown to promote in vivo growth of xenografted MM cells harboring p53 mutation in mice. Since activity of the APRIL/BCMA pathway plays a central role in MM pathogenesis and drug resistance via bidirectional interactions between tumor cells and their supporting bone marrow microenvironment, BCMA has been identified as a target for the treatment of MM. For further details see, e.g., Yu-Tsu Tai et al., Blood 2016; 127(25):3225-3236.

Another B-cell disorder involving plasma cells expressing BCMA is systemic lupus erythematosus (SLE), also known as lupus. SLE is a systemic, autoimmune disease that can affect any part of the body and is represented with the immune system attacking the body's own cells and tissue, resulting in chronic inflammation and tissue damage. It is a Type III hypersensitivity reaction in which antibody-immune complexes precipitate and cause a further immune response (Inaki & Lee, Nat Rev Rheumatol 2010; 6: 326-337).

The anti-BCMA heavy chain-only antibodies (UniAbs) of the present invention can be used to develop therapeutic agents for the treatment of MM, SLE, and other B-cell disorders or plasma cell disorders characterized by the expression of BCMA, such as those listed above. In particular, the anti-BCMA heavy chain-only antibodies (UniAbs) of the present invention are candidates for the treatment of MM, alone or in combination with other MM treatments.

In one embodiment, the antibodies herein can be in the form of heavy chain-only anti-BCMA antibody-CAR structures, i.e., heavy chain-only anti-BCMA antibody-CAR-transduced T cell structures.

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage of the agent may range from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg. An exemplary treatment regimen entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g., lyophilized) compositions. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans. The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents of the invention, and formulations thereof, and instructions for use. The kits can further contain a least one additional reagent, e.g., a chemotherapeutic drug, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention.

EXAMPLES

Example 1

Genetically Engineered Rats Expressing Heavy Chain-Only Antibodies

A 'human—rat' IgH locus was constructed and assembled in several parts. This involved the modification and joining of rat C region genes downstream of human JHs and subsequently, the upstream addition of the human VH6-D-segment region. Two BACs with separate clusters of human VH genes [BAC6 and BAC3] were then co-injected with the BAC termed Georg, encoding the assembled and modified region comprising human VH6, all Ds, all JHs, and modified rat Cγ2a/1/2b (ΔCH1).

Transgenic rats carrying artificial heavy chain immunoglobulin loci in unrearranged configuration were generated. The IgG2a($\Delta C_H$ 1)., igG1($\Delta C_H$ 1)., IgG2b($\Delta C_H$ 1) genes lacked the CH segment. The constant region genes IgE, IgA and 3' enhancer were included in Georg BAC. RT-PCR and serum analysis (ELISA) of transgenic rats revealed productive rearrangement of transgenic immunoglobulin loci and expression of heavy chain only antibodies of various isotypes in serum. Transgenic rats were cross-bred with rats with mutated endogenous heavy chain and light chain loci previously described in US patent publication 2009/0098134 A1. Analysis of such animals demonstrated inactivation of rat immunoglobulin heavy and light chain expression and high level expression of heavy chain antibodies with variable regions encoded by human V, D, and J genes. Immunization of transgenic rats resulted in production of high titer serum responses of antigen-specific heavy chain antibodies. These transgenic rats expressing heavy chain antibodies with a human VDJ region were called UniRats.

Example 2

Immunization
Immunization with Recombinant Extracellular Domain of BCMA.

Twelve UniRat animals (6 HC27, 6 HC28) were immunized with recombinant human BCMA protein. The animals were immunized according to standard protocol using a Titermax/Alhydrogel adjuvant. Recombinant extracellular domain of BCMA was purchased from R&D Systems and was diluted with sterile saline and combined with adjuvant. The immunogen was combined with Titermax and Alhydrogel adjuvants. The first immunization (priming) with immunogen in Titermax was administered in the left and right legs. Subsequent boosting immunizations were done in the presence of Alhydrogel and three days before harvest boosts were performed with immunogens in PBS. Serum was collected from rats at the final bleed to determine serum titers.

Serum Titer Results
Binding activity for a single 1:500 serum titer dilution is tested by ELISA against a huBCMA+Fc protein and a cynoBCMA+Fc protein produced in eukaryotic cells and two human BCMA proteins from E. coli and wheat germ, respectively. In addition, serum samples are tested against two off-target proteins, HSA and human IgG1. In addition, serum from all animals is assayed for binding to NCI-H929 cells (BCMA+, lambda−).

Since usually a significant spread of results is observed in serum reactivity levels to NCI-H929 cells (BCMA+, lambda−), the relevance of these results is confirmed by the ELISA binding data generated for a subset of the animals. Positive signal for binding to the cynoBCMA+Fc protein may reflect binding to either the ECD or the Fc portion of the molecule that is also included on the human immunogen. In both assay types, analysis of serum taken from these animals prior to immunization showed no reactivity to the immunogen or off target protein.

Example 3

Gene Assembly, Expression and Binding Assays
cDNAs encoding heavy chain only antibodies highly expressed in lymph node cells were selected for gene assembly and cloned into an expression vector. Subsequently, these heavy chain sequences were expressed in HEK cells as UniAb heavy chain only antibodies (CH1 deleted, no light chain).

The results of assays testing the binding of the anti-BCMA heavy chain-only antibodies of the invention to BCMA protein (human and cynomolgus) and a BCMA-expressing cell line (H929; BCMA+, lambda−) at various concentrations are shown in FIG. 4. The NCI-H929 cell line is human multiple myeloma line expressing human BCMA, which was obtained from the American Type Culture Collection (ATCC) and cultured according to ATCC recommendations.

Supernatants of 4 antibodies were tested for binding in a standard ELISA assay to human and cynomolgus BCMA. Binding to recombinant BCMA protein was determined by ELISA using human BCMA ECD obtained from Abcam (ab50089). The BCMA ECD protein was used at a concentration of 2 g/mL to capture UniAbs at 50 ng/mL. Binding of UniAbs was detected with a goat anti-human IgG HRP conjugated antibody (ThermoFisher 31413). All antibodies were diluted in 1×TBS with 0.05% Tween-20 and 1% dry milk powder.

Off-target binding of human IgG1 was assessed by ELISA using the UniAbs to capture human IgG1 kappa followed by detection of the kappa chain with a goat anti-human kappa HRP conjugated antibody (Southern Biotech 2060-05).

Supernatants of the 4 test anti-BCMA antibodies were also tested by flow cytometry for binding to H929 cells. The samples were measured by flow cytometry using a Guava easyCyte 8HT instrument from EMD Millipore and analyzed using guavaSoft. Bound antibodies were detected with goat anti-human IgG F(ab)2 conjugated to PE (Southern Biotech 2042-09). All antibodies were diluted in PBS with 1% BSA. Positive staining was determined by comparison to staining with a human IgG1 isotype control.

In FIG. 4: Column 1 indicates the clone ID of the HCAb. Column 2 indicates the family ID of the HCAb based on the CDR3 sequence. Column 3 indicates the CDR1 amino acid sequence. Column 4 indicates the CDR2 amino acid sequence. Column 5 indicates the CDR3 amino acid sequence. Column 6 indicates the concentration of the expressed HCAb in ug/mL. Column 7 indicates the mean fluorescent intensity of cell binding to H929 human cells that express BCMA. Column 8 indicates the mean fluorescent intensity of cell binding to CHO cells that express cyno BCMA. Column 9 indicates the ELISA fold over background signal of human BCMA protein binding. Column 10 indicates the ELISA fold over background signal of cyno BCMA protein binding. Column 11 indicates the ELISA fold over background signal of lambda protein binding, an off-target control. Column 12 indicates the ELISA fold over background signal of a multi-tag protein binding, an off-target control. Column 13 indicates the binding off-rate to human BCMA protein measured by the Octet. Column 14 indicates the binding off-rate to cyno BCMA protein measured by the Octet.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A heavy chain-only antibody binding to human B-Cell Maturation Antigen (BCMA) comprising a heavy chain variable region comprising:
   (i) a CDR1 sequence of SEQ ID NO: 1, a CDR2 sequence of SEQ ID NO: 4, and a CDR3 sequence of SEQ ID NO: 8; or
   (ii) a CDR1 sequence of SEQ ID NO: 2, a CDR2 sequence of SEQ ID NO: 5, and a CDR3 sequence of SEQ ID NO: 9; or
   (iii) a CDR1 sequence of SEQ ID NO: 2, a CDR2 sequence of SEQ ID NO: 6, and a CDR3 sequence of SEQ ID NO: 10; or
   (iv) a CDR1 sequence of SEQ ID NO: 3, a CDR2 sequence of SEQ ID NO: 7, and a CDR3 sequence of SEQ ID NO: 11.

2. The heavy chain-only antibody of claim 1, wherein said CDR1, CDR2, and CDR3 sequences are present in a human framework.

3. The heavy chain-only antibody of claim 1, further comprising a heavy chain constant region sequence in the absence of a CH1 sequence.

4. The heavy chain-only antibody of claim 1, comprising a heavy chain variable region having at least 95% sequence identity to SEQ ID NO: 15.

5. The heavy chain-only antibody of claim 4, comprising a heavy chain variable region sequence comprising SEQ ID NO: 15.

6. The heavy chain-only antibody of claim 1, which is multi-specific.

7. The heavy chain-only antibody of claim 6, which is bispecific.

8. The heavy chain-only antibody of claim 6, having binding affinity to an effector cell.

9. The heavy chain-only antibody of claim 6, having binding affinity to a T-cell antigen.

10. The heavy chain-only antibody of claim 9, having binding affinity to CD3.

11. The heavy chain-only antibody of claim 1, which is in a CAR-T format.

12. The heavy chain-only antibody of claim 11, which is present in a CAR-transduced T-cell.

13. A T-cell transduced with the heavy chain-only antibody of claim 11.

14. A pharmaceutical composition comprising a heavy chain-only antibody of claim 1.

* * * * *

UNITED STATES PATENT AND TRADEMARK OFFICE
CERTIFICATE OF CORRECTION

| | | |
|---|---|---|
| PATENT NO. | : 11,970,540 B2 | Page 1 of 1 |
| APPLICATION NO. | : 16/622881 | |
| DATED | : April 30, 2024 | |
| INVENTOR(S) | : Trinklein et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 627 days.

Signed and Sealed this
Twelfth Day of August, 2025

Coke Morgan Stewart
*Acting Director of the United States Patent and Trademark Office*